(12) United States Patent
Wiener et al.

(10) Patent No.: US 8,257,377 B2
(45) Date of Patent: Sep. 4, 2012

(54) MULTIPLE END EFFECTORS ULTRASONIC SURGICAL INSTRUMENTS

(75) Inventors: Eitan T. Wiener, Cincinnati, OH (US); Matthew C. Miller, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 352 days.

(21) Appl. No.: 11/881,654

(22) Filed: Jul. 27, 2007

(65) Prior Publication Data

US 2009/0030351 A1 Jan. 29, 2009

(51) Int. Cl.
*A61B 17/32* (2006.01)

(52) U.S. Cl. .................................................. 606/169

(58) Field of Classification Search .............. 606/37, 606/39, 40, 45, 49, 169, 170, 171; 601/2; 604/22; 433/43, 51, 52, 86, 118, 119, 141, 433/142, 143, 144; 30/162, 140
See application file for complete search history.

(56) References Cited

U.S. PATENT DOCUMENTS

| | | | |
|---|---|---|---|
| 2,736,960 A * | 3/1956 | Armstrong | 30/162 |
| 2,849,788 A | 9/1958 | Creek | |
| 3,015,961 A | 1/1962 | Roney | |
| 3,526,219 A | 9/1970 | Balamuth | |
| 3,636,943 A | 1/1972 | Balamuth | |
| 3,776,238 A | 12/1973 | Peyman et al. | |
| 3,805,787 A | 4/1974 | Banko | |
| 3,862,630 A | 1/1975 | Balamuth | |
| 3,900,823 A | 8/1975 | Sokal et al. | |
| 3,918,442 A | 11/1975 | Nikolaev et al. | |
| 3,956,826 A | 5/1976 | Perdreaux, Jr. | |
| 4,156,187 A | 5/1979 | Murry et al. | |
| 4,200,106 A | 4/1980 | Douvas et al. | |
| 4,445,063 A | 4/1984 | Smith | |
| 4,491,132 A | 1/1985 | Aikins | |
| 4,634,420 A | 1/1987 | Spinosa et al. | |
| 4,640,279 A | 2/1987 | Beard | |
| 4,708,127 A | 11/1987 | Abdelghani | |
| 4,832,683 A | 5/1989 | Idemoto et al. | |
| 4,838,853 A | 6/1989 | Parisi | |
| 4,850,354 A | 7/1989 | McGurk-Burleson et al. | |
| 4,865,159 A | 9/1989 | Jamison | |
| 4,896,009 A | 1/1990 | Pawlowski | |
| 4,922,902 A | 5/1990 | Wuchinich et al. | |

(Continued)

FOREIGN PATENT DOCUMENTS

EP 0443256 A1 8/1991

(Continued)

OTHER PUBLICATIONS

Technology Overview, printed from www.harmonicscalpel.com, Internet site, website accessed on Jun. 13, 2007, (3 pages).

(Continued)

*Primary Examiner* — Elizabeth Houston
*Assistant Examiner* — Jonathan W Miles

(57) ABSTRACT

A surgical instrument includes a transducer configured to produce vibrations along a longitudinal axis at a predetermined frequency. The transducer includes a first end and a second end. A first resonator portion includes a first end coupled to the first end of the transducer. The first resonator includes a second end adapted to receive a first ultrasonic transmission waveguide. A second resonator portion includes a first end coupled to the second end of the transducer. The second resonator includes a second end adapted to receive a second ultrasonic transmission waveguide.

9 Claims, 16 Drawing Sheets

U.S. PATENT DOCUMENTS

| | | |
|---|---|---|
| 4,981,756 A | 1/1991 | Rhandhawa |
| 5,026,387 A | 6/1991 | Thomas |
| 5,112,300 A | 5/1992 | Ureche |
| 5,123,903 A | 6/1992 | Quaid et al. |
| 5,162,044 A | 11/1992 | Gahn et al. |
| 5,167,725 A | 12/1992 | Clark et al. |
| 332,660 A | 1/1993 | Rawson et al. |
| 5,176,695 A | 1/1993 | Dulebohn |
| 5,184,605 A | 2/1993 | Grzeszykowski |
| 5,213,569 A | 5/1993 | Davis |
| 5,221,282 A | 6/1993 | Wuchinich |
| 5,226,910 A | 7/1993 | Kajiyama et al. |
| 5,241,236 A | 8/1993 | Sasaki et al. |
| 5,257,988 A | 11/1993 | L'Esperance, Jr. |
| 5,261,922 A | 11/1993 | Hood |
| 5,263,957 A | 11/1993 | Davison |
| 5,282,800 A | 2/1994 | Foshee et al. |
| 347,474 A | 5/1994 | Olson |
| 5,322,055 A | 6/1994 | Davison et al. |
| 5,324,299 A | 6/1994 | Davison et al. |
| 5,346,502 A | 9/1994 | Estabrook et al. |
| 5,366,466 A | 11/1994 | Christian et al. |
| 354,564 A | 1/1995 | Medema |
| 5,411,481 A | 5/1995 | Allen et al. |
| 5,419,761 A | 5/1995 | Narayanan et al. |
| 5,421,829 A | 6/1995 | Olichney et al. |
| 5,449,370 A | 9/1995 | Vaitekunas |
| 5,483,501 A | 1/1996 | Park et al. |
| 5,486,162 A | 1/1996 | Brumbach |
| 5,500,216 A | 3/1996 | Julian et al. |
| 5,501,654 A | 3/1996 | Failla et al. |
| 5,505,693 A | 4/1996 | Mackool |
| 5,562,609 A | 10/1996 | Brumbach |
| 5,562,610 A | 10/1996 | Brumbach |
| 5,601,601 A | 2/1997 | Tal et al. |
| 5,607,436 A | 3/1997 | Pratt et al. |
| 5,618,492 A | 4/1997 | Auten et al. |
| 5,628,760 A | 5/1997 | Knoepfler |
| 5,630,420 A | 5/1997 | Vaitekunas |
| 381,077 A | 7/1997 | Hunt |
| 5,653,713 A | 8/1997 | Michelson |
| 5,669,922 A | 9/1997 | Hood |
| 5,674,235 A | 10/1997 | Parisi |
| 5,690,269 A | 11/1997 | Bolanos et al. |
| 5,694,936 A | 12/1997 | Fujimoto et al. |
| 5,713,896 A | 2/1998 | Nardella |
| 5,741,226 A | 4/1998 | Strukel et al. |
| 5,810,859 A | 9/1998 | DiMatteo et al. |
| 5,827,323 A | 10/1998 | Klieman et al. |
| 5,828,160 A | 10/1998 | Sugishita |
| 5,843,109 A | 12/1998 | Mehta et al. |
| 5,879,364 A | 3/1999 | Bromfield et al. |
| 5,893,835 A | 4/1999 | Witt et al. |
| 5,897,569 A | 4/1999 | Kellogg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,943 A | 9/1999 | Vaitekunas |
| 5,968,007 A | 10/1999 | Simon et al. |
| 5,968,060 A | 10/1999 | Kellogg |
| 416,089 A | 11/1999 | Barton et al. |
| 5,989,274 A | 11/1999 | Davison et al. |
| 5,989,275 A | 11/1999 | Estabrook et al. |
| 5,993,972 A | 11/1999 | Reich et al. |
| 6,033,375 A | 3/2000 | Brumbach |
| 6,063,098 A | 5/2000 | Houser et al. |
| 6,066,132 A | 5/2000 | Chen et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,109,500 A | 8/2000 | Alli et al. |
| 6,113,594 A | 9/2000 | Savage |
| 6,139,320 A | 10/2000 | Hahn |
| 6,152,902 A | 11/2000 | Christian et al. |
| 6,159,160 A | 12/2000 | Hsei et al. |
| 6,159,175 A | 12/2000 | Strukel et al. |
| 6,206,844 B1 | 3/2001 | Reichel et al. |
| 6,210,403 B1 | 4/2001 | Klicek |
| 6,214,023 B1 | 4/2001 | Whipple et al. |
| 6,233,476 B1 | 5/2001 | Strommer et al. |
| 6,238,366 B1 | 5/2001 | Savage et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,352,532 B1 | 3/2002 | Kramer et al. |
| 6,379,320 B1 | 4/2002 | Lafon et al. |
| 6,383,194 B1 | 5/2002 | Pothula |
| 6,387,109 B1 | 5/2002 | Davison et al. |
| 6,391,042 B1 | 5/2002 | Cimino |
| 6,416,486 B1 | 7/2002 | Wampler |
| 6,423,073 B2 | 7/2002 | Bowman |
| 6,423,082 B1 | 7/2002 | Houser et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,524,316 B1 | 2/2003 | Nicholson et al. |
| 6,533,784 B2 | 3/2003 | Truckai et al. |
| 6,537,291 B2 | 3/2003 | Friedman et al. |
| 6,543,456 B2 | 4/2003 | Freeman |
| 6,544,260 B1 | 4/2003 | Markel et al. |
| 6,561,983 B2 | 5/2003 | Cronin et al. |
| 6,572,632 B2 | 6/2003 | Zisterer et al. |
| 6,575,969 B1 | 6/2003 | Rittman, III et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,656,177 B2 | 12/2003 | Truckai et al. |
| 6,662,127 B2 | 12/2003 | Wiener et al. |
| 6,663,941 B2 | 12/2003 | Brown et al. |
| 6,676,660 B2 | 1/2004 | Wampler et al. |
| 6,678,621 B2 | 1/2004 | Wiener et al. |
| 6,679,899 B2 | 1/2004 | Wiener et al. |
| 6,682,544 B2 | 1/2004 | Mastri et al. |
| 6,716,215 B1 | 4/2004 | David et al. |
| 6,733,506 B1 | 5/2004 | McDevitt et al. |
| 6,770,072 B1 | 8/2004 | Truckai et al. |
| 6,773,444 B2 | 8/2004 | Messerly |
| 6,786,383 B2 | 9/2004 | Stegelmann |
| 6,790,216 B1 | 9/2004 | Ishikawa |
| 6,802,843 B2 | 10/2004 | Truckai et al. |
| 6,828,712 B2 | 12/2004 | Battaglin et al. |
| 6,869,439 B2 | 3/2005 | White et al. |
| 6,875,220 B2 | 4/2005 | Du et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,926,716 B2 | 8/2005 | Baker et al. |

| | | | | | | |
|---|---|---|---|---|---|---|
| 6,929,632 B2 | 8/2005 | Nita et al. | 2004/0097996 A1 | 5/2004 | Rabiner et al. | |
| 6,929,644 B2 | 8/2005 | Truckai et al. | 2004/0199193 A1 | 10/2004 | Hayashi et al. | |
| D509,589 S | 9/2005 | Wells | 2004/0204728 A1 | 10/2004 | Haefner | |
| 6,945,981 B2 | 9/2005 | Donofrio et al. | 2004/0260300 A1 | 12/2004 | Gorensek et al. | |
| D511,145 S | 11/2005 | Donofrio et al. | 2005/0049546 A1 | 3/2005 | Messerly et al. | |
| 6,976,969 B2 | 12/2005 | Messerly | 2005/0143769 A1 | 6/2005 | White et al. | |
| 6,977,495 B2 | 12/2005 | Donofrio | 2005/0165345 A1 | 7/2005 | Laufer et al. | |
| 6,984,220 B2 | 1/2006 | Wuchinich | 2005/0177184 A1 | 8/2005 | Easley | |
| 7,011,657 B2 | 3/2006 | Truckai et al. | 2005/0192610 A1 | 9/2005 | Houser et al. | |
| 7,041,088 B2 | 5/2006 | Nawrocki et al. | 2005/0209620 A1 | 9/2005 | Du et al. | |
| 7,041,102 B2 | 5/2006 | Truckai et al. | 2005/0261581 A1 | 11/2005 | Hughes et al. | |
| 7,070,597 B2 | 7/2006 | Truckai et al. | 2005/0261588 A1 | 11/2005 | Makin et al. | |
| 7,074,219 B2 | 7/2006 | Levine et al. | 2005/0288659 A1 | 12/2005 | Kimura et al. | |
| 7,077,039 B2 | 7/2006 | Gass et al. | 2006/0030797 A1 | 2/2006 | Zhou et al. | |
| 7,077,853 B2 | 7/2006 | Kramer et al. | 2006/0063130 A1* | 3/2006 | Hayman et al. | 433/141 |
| 7,083,619 B2 | 8/2006 | Truckai et al. | 2006/0079784 A1 | 4/2006 | Houser | |
| 7,087,054 B2 | 8/2006 | Truckai et al. | 2006/0084963 A1 | 4/2006 | Messerly | |
| 7,108,695 B2 | 9/2006 | Witt et al. | 2006/0190034 A1 | 8/2006 | Nishizawa et al. | |
| 7,112,201 B2 | 9/2006 | Truckai et al. | 2006/0211943 A1 | 9/2006 | Beaupre | |
| 7,118,564 B2 | 10/2006 | Ritchie et al. | 2006/0235306 A1 | 10/2006 | Cotter et al. | |
| 7,125,409 B2 | 10/2006 | Truckai et al. | 2006/0253050 A1 | 11/2006 | Yoshimine et al. | |
| 7,135,018 B2 | 11/2006 | Ryan et al. | 2007/0016235 A1 | 1/2007 | Tanaka et al. | |
| 7,135,030 B2 | 11/2006 | Schwemberger et al. | 2007/0016236 A1 | 1/2007 | Beaupre | |
| 7,153,315 B2 | 12/2006 | Miller | 2007/0055228 A1 | 3/2007 | Berg et al. | |
| 7,156,189 B1 | 1/2007 | Bar-Cohen et al. | 2007/0060915 A1 | 3/2007 | Kucklick | |
| 7,156,853 B2 | 1/2007 | Muratsu | 2007/0063618 A1 | 3/2007 | Bromfield | |
| 7,157,058 B2 | 1/2007 | Marhasin et al. | 2007/0129716 A1 | 6/2007 | Daw et al. | |
| 7,159,750 B2 | 1/2007 | Racenet et al. | 2007/0130771 A1 | 6/2007 | Ehlert et al. | |
| 7,163,548 B2 | 1/2007 | Stulen et al. | 2007/0131034 A1 | 6/2007 | Ehlert et al. | |
| 7,169,146 B2 | 1/2007 | Truckai et al. | 2007/0149881 A1 | 6/2007 | Rabin | |
| 7,179,271 B2 | 2/2007 | Friedman et al. | 2007/0162050 A1 | 7/2007 | Sartor | |
| 7,186,253 B2 | 3/2007 | Truckai et al. | 2007/0173872 A1 | 7/2007 | Neuenfeldt | |
| 7,189,233 B2 | 3/2007 | Truckai et al. | 2007/0185380 A1 | 8/2007 | Kucklick | |
| 7,204,820 B2 | 4/2007 | Akahoshi | 2007/0219481 A1 | 9/2007 | Babaev | |
| 7,220,951 B2 | 5/2007 | Truckai et al. | 2007/0249941 A1 | 10/2007 | Salehi et al. | |
| 7,223,229 B2 | 5/2007 | Inman et al. | 2007/0265560 A1 | 11/2007 | Soltani et al. | |
| 7,229,455 B2 | 6/2007 | Sakurai et al. | 2007/0275348 A1 | 11/2007 | Lemon | |
| 7,273,483 B2 | 9/2007 | Wiener et al. | 2007/0282335 A1 | 12/2007 | Young et al. | |
| 7,309,849 B2 | 12/2007 | Truckai et al. | 2007/0287933 A1 | 12/2007 | Phan et al. | |
| 7,311,709 B2 | 12/2007 | Truckai et al. | 2008/0009848 A1 | 1/2008 | Paraschiv et al. | |
| 7,326,236 B2 | 2/2008 | Andreas et al. | 2008/0058585 A1 | 3/2008 | Novak et al. | |
| 7,331,410 B2 | 2/2008 | Yong et al. | 2008/0058775 A1 | 3/2008 | Darian et al. | |
| 7,354,440 B2 | 4/2008 | Truckal et al. | 2008/0058845 A1 | 3/2008 | Shimizu et al. | |
| 7,380,695 B2 | 6/2008 | Doll et al. | 2008/0082039 A1 | 4/2008 | Babaev | |
| 7,381,209 B2 | 6/2008 | Truckai et al. | 2008/0082098 A1 | 4/2008 | Tanaka et al. | |
| 7,390,317 B2 | 6/2008 | Taylor et al. | 2008/0172051 A1 | 7/2008 | Masuda et al. | |
| 7,408,288 B2 | 8/2008 | Hara | 2008/0177268 A1 | 7/2008 | Daum et al. | |
| D576,725 S | 9/2008 | Shumer et al. | 2008/0188878 A1 | 8/2008 | Young | |
| D578,643 S | 10/2008 | Shumer et al. | 2008/0200940 A1 | 8/2008 | Eichmann et al. | |
| D578,644 S | 10/2008 | Shumer et al. | 2008/0208231 A1 | 8/2008 | Ota et al. | |
| D578,645 S | 10/2008 | Shumer et al. | 2008/0234708 A1 | 9/2008 | Houser et al. | |
| 7,431,704 B2 | 10/2008 | Babaev | 2008/0234709 A1 | 9/2008 | Houser | |
| 7,472,815 B2 | 1/2009 | Shelton, IV et al. | 2008/0234710 A1 | 9/2008 | Neurohr et al. | |
| 7,479,148 B2 | 1/2009 | Beaupre | 2008/0234711 A1 | 9/2008 | Houser et al. | |
| 7,479,160 B2 | 1/2009 | Branch et al. | 2008/0262490 A1 | 10/2008 | Williams | |
| 7,503,893 B2 | 3/2009 | Kucklick | 2008/0281200 A1 | 11/2008 | Voic et al. | |
| 7,534,243 B1 | 5/2009 | Chin et al. | 2008/0287948 A1 | 11/2008 | Newton et al. | |
| D594,983 S | 6/2009 | Price et al. | 2009/0030311 A1 | 1/2009 | Stulen et al. | |
| 7,567,012 B2 | 7/2009 | Namikawa | 2009/0030437 A1 | 1/2009 | Houser et al. | |
| D618,797 S | 6/2010 | Price et al. | 2009/0030438 A1 | 1/2009 | Stulen | |
| 7,751,115 B2 | 7/2010 | Song | 2009/0030439 A1 | 1/2009 | Stulen | |
| 7,770,774 B2 | 8/2010 | Mastri et al. | 2009/0036911 A1 | 2/2009 | Stulen | |
| 7,780,659 B2 | 8/2010 | Okada et al. | 2009/0036912 A1 | 2/2009 | Wiener et al. | |
| D631,965 S | 2/2011 | Price et al. | 2009/0036913 A1 | 2/2009 | Wiener et al. | |
| 2001/0025184 A1 | 9/2001 | Messerly | 2009/0036914 A1 | 2/2009 | Houser | |
| 2001/0031950 A1 | 10/2001 | Ryan | 2009/0076506 A1 | 3/2009 | Baker | |
| 2001/0039419 A1 | 11/2001 | Francischelli et al. | 2009/0082716 A1 | 3/2009 | Akahoshi | |
| 2002/0002377 A1 | 1/2002 | Cimino | 2009/0105750 A1 | 4/2009 | Price et al. | |
| 2002/0019649 A1 | 2/2002 | Sikora et al. | 2009/0118802 A1 | 5/2009 | Mioduski et al. | |
| 2002/0022836 A1 | 2/2002 | Goble et al. | 2009/0143795 A1 | 6/2009 | Robertson | |
| 2002/0077550 A1 | 6/2002 | Rabiner et al. | 2009/0143796 A1 | 6/2009 | Stulen et al. | |
| 2002/0156493 A1 | 10/2002 | Houser et al. | 2009/0143806 A1 | 6/2009 | Witt et al. | |
| 2003/0055443 A1 | 3/2003 | Spotnitz | 2010/0036370 A1 | 2/2010 | Mirel et al. | |
| 2003/0204199 A1 | 10/2003 | Novak et al. | 2010/0036405 A1 | 2/2010 | Giordano et al. | |
| 2003/0212332 A1 | 11/2003 | Fenton et al. | 2010/0179577 A1 | 7/2010 | Houser | |
| 2004/0030254 A1 | 2/2004 | Babaev | 2010/0187283 A1 | 7/2010 | Crainich et al. | |
| 2004/0047485 A1 | 3/2004 | Sherrit et al. | 2010/0298743 A1 | 11/2010 | Nield et al. | |
| 2004/0092921 A1 | 5/2004 | Kadziauskas et al. | 2010/0298851 A1 | 11/2010 | Nield | |
| 2004/0097919 A1 | 5/2004 | Wellman et al. | 2010/0331869 A1 | 12/2010 | Voegele et al. | |

| | | | |
|---|---|---|---|
| 2010/0331870 A1 | 12/2010 | Wan et al. | |
| 2010/0331871 A1 | 12/2010 | Nield et al. | |
| 2010/0331872 A1 | 12/2010 | Houser et al. | |
| 2011/0015627 A1 | 1/2011 | Dinardo et al. | |
| 2011/0015631 A1 | 1/2011 | Wiener et al. | |
| 2011/0015660 A1 | 1/2011 | Wiener et al. | |
| 2011/0082486 A1 | 4/2011 | Messerly et al. | |
| 2011/0087212 A1 | 4/2011 | Aldridge et al. | |
| 2011/0087213 A1 | 4/2011 | Messerly et al. | |
| 2011/0087214 A1 | 4/2011 | Giordano et al. | |
| 2011/0087215 A1 | 4/2011 | Aldridge et al. | |
| 2011/0087216 A1 | 4/2011 | Aldridge et al. | |
| 2011/0087217 A1 | 4/2011 | Yates et al. | |
| 2011/0087256 A1 | 4/2011 | Wiener et al. | |
| 2011/0125175 A1 | 5/2011 | Stulen et al. | |

FOREIGN PATENT DOCUMENTS

| | | |
|---|---|---|
| EP | 0456470 A1 | 11/1991 |
| EP | 0482195 B1 | 4/1992 |
| EP | 0612570 B1 | 6/1997 |
| EP | 0908148 B1 | 1/2002 |
| EP | 1199044 B1 | 12/2005 |
| EP | 1844720 A1 | 10/2007 |
| EP | 1862133 A1 | 12/2007 |
| EP | 1974771 A1 | 10/2008 |
| EP | 1832259 B1 | 6/2009 |
| EP | 2074959 A1 | 7/2009 |
| WO | WO 92/22259 A2 | 12/1992 |
| WO | WO 98/37815 A1 | 9/1998 |
| WO | WO 01/54590 A1 | 8/2001 |
| WO | WO 2005/122917 A1 | 12/2005 |
| WO | WO 2006/042210 A2 | 4/2006 |
| WO | WO 2006/129465 A1 | 12/2006 |
| WO | WO 2007/047531 A2 | 4/2007 |
| WO | WO 2007/143665 A2 | 12/2007 |
| WO | WO 2009/027065 A1 | 3/2009 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

AST Products, Inc., "Principles of Video Contact Angle Analysis," 20 pages, (date unknown).

Lim et al., "A Review of Mechanism Used in Laparoscopic Surgical Instruments," Mechanism and Machine Theory, vol. 38, pp. 1133-1147, (2003).

International Search Report for PCT/US2008/070992, Nov. 7, 2008 (4 pages).

Gooch et al., "Recommended Infection-Control Practices for Dentistry, 1993," Published: May 28, 1993; [retrieved on Aug. 23, 2008]. Retrieved from the Internet: URL: http//wonder.cdc.gov/wonder/prevguid/p0000191/p0000191.asp (15 pages).

U.S. Appl. No. 12/181,816, filed Jul. 29, 2008.
U.S. Appl. No. 11/881,602, filed Jul. 27, 2007.
U.S. Appl. No. 11/888,081, filed Jul. 31, 2007.
U.S. Appl. No. 11/881,636, filed Jul. 27, 2007.
U.S. Appl. No. 11/881,645, filed Jul. 27, 2007.
U.S. Appl. No. 11/888,171, filed Jul. 31, 2007.
U.S. Appl. No. 11/998,758, filed Nov. 30, 2007.
U.S. Appl. No. 11/881,662, filed Jul. 27, 2007.
U.S. Appl. No. 11/888,222, filed Jul. 31, 2007.
U.S. Appl. No. 12/245,158, filed Oct. 3, 2008.
U.S. Appl. No. 29/292,295, filed Oct. 5, 2007.
U.S. Appl. No. 11/998,543, filed Nov. 30, 2007.
U.S. Appl. No. 29/327,737, filed Nov. 12, 2008.

AST Products, Inc., "Principles of Video Contact Angle Analysis," 20 pages, (2006).

U.S. Appl. No. 12/469,293, filed May 20, 2009.
U.S. Appl. No. 12/469,308, filed May 20, 2009.
U.S. Appl. No. 12/503,769, filed Jul. 15, 2009.
U.S. Appl. No. 12/503,770, filed Jul. 15, 2009.
U.S. Appl. No. 12/503,766, filed Jul. 15, 2009.
U.S. Appl. No. 12/490,906, filed Jun. 24, 2009.
U.S Appl. No. 12/490,922, filed Jun. 24, 2009.
U.S. Appl. No. 12/490,933, filed Jun. 24, 2009.
U.S. Appl. No. 12/490,948, filed Jun. 24, 2009.
U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.
U.S. Appl. No. 12/703,899, filed Feb. 11, 2010.
U.S. Appl. No. 29/361,917, filed May 17, 2010.
U.S. Appl. No. 12/896,351, filed Oct. 1, 2010.
U.S. Appl. No. 12/896,479, filed Oct. 1, 2010.
U.S. Appl. No. 12/896,360, filed Oct. 1, 2010.
U.S. Appl. No. 12/896,345, filed Oct. 1, 2010.
U.S. Appl. No. 12/896,384, filed Oct. 1, 2010.
U.S. Appl. No. 12/896,467, filed Oct. 1, 2010.
U.S. Appl. No. 12/896,451, filed Oct. 1, 2010.
U.S. Appl. No. 12/896,470, filed Oct. 1, 2010.
U.S. Appl. No. 12/896,411, filed Oct. 1, 2010.
U.S. Appl. No. 12/896,420, filed Oct. 1, 2010.

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Incropera et al., Fundamentals of Heat and Mass Transfer, Wiley, New York (1990). (Book—not attached).

F. A. Duck, "Optical Properties of Tissue Including Ultraviolet and Infrared Radiation," pp. 43-71 in *Physical Properties of Tissue* (1990).

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

Campbell et al, "Thermal Imaging in Surgery," p. 19-3, in *Medical Infrared Imaging*, N. A. Diakides and J. D. Bronzino, Eds. (2008).

* cited by examiner

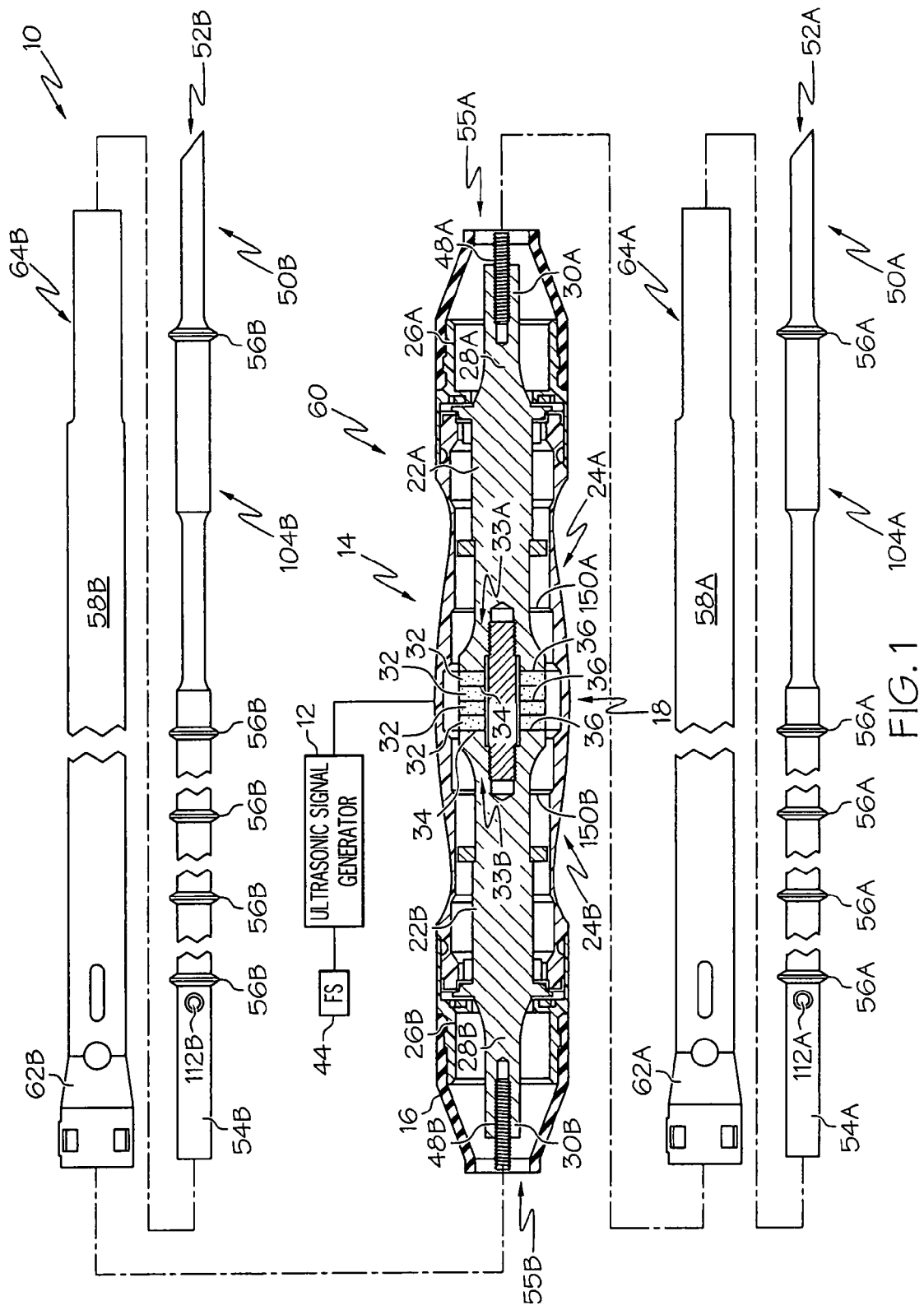

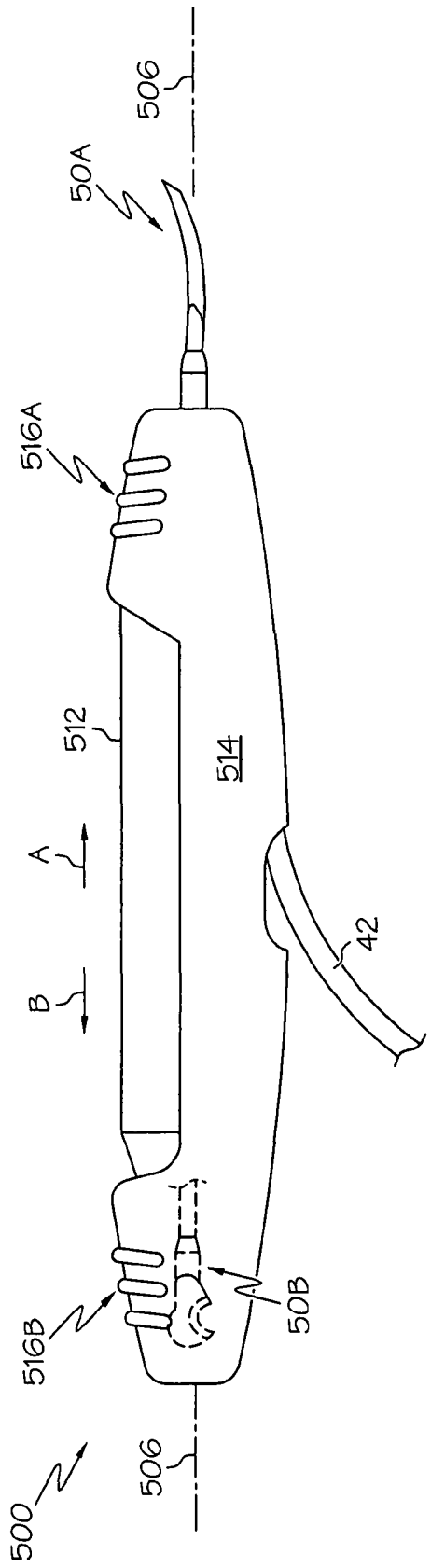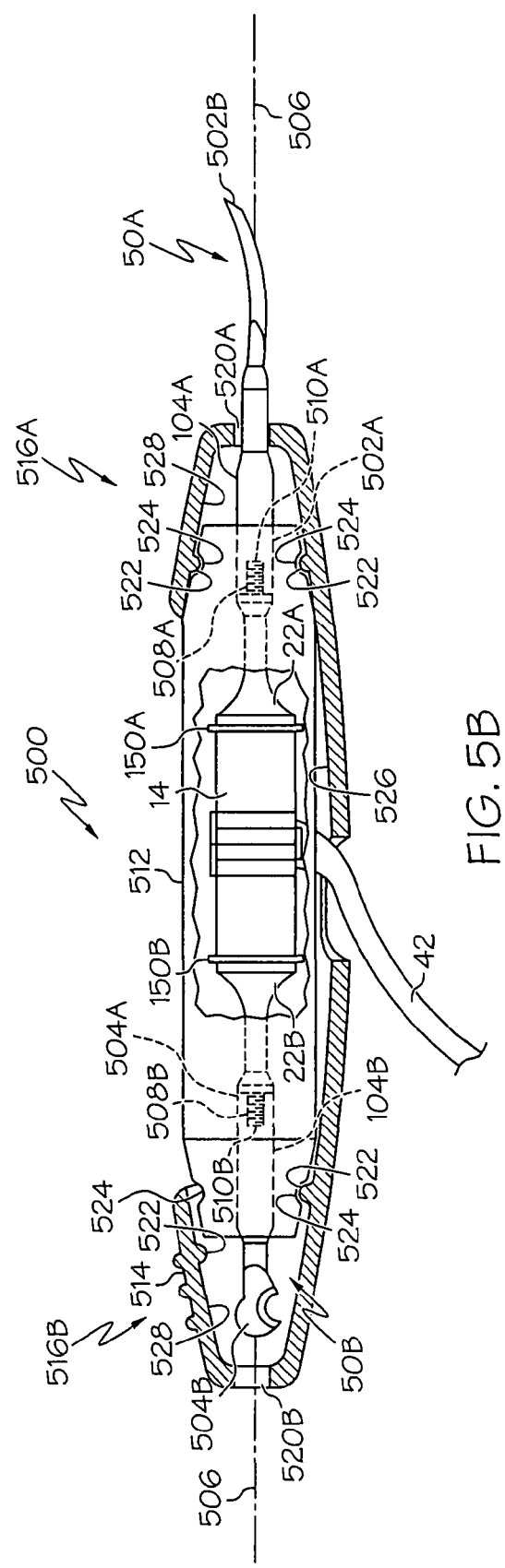

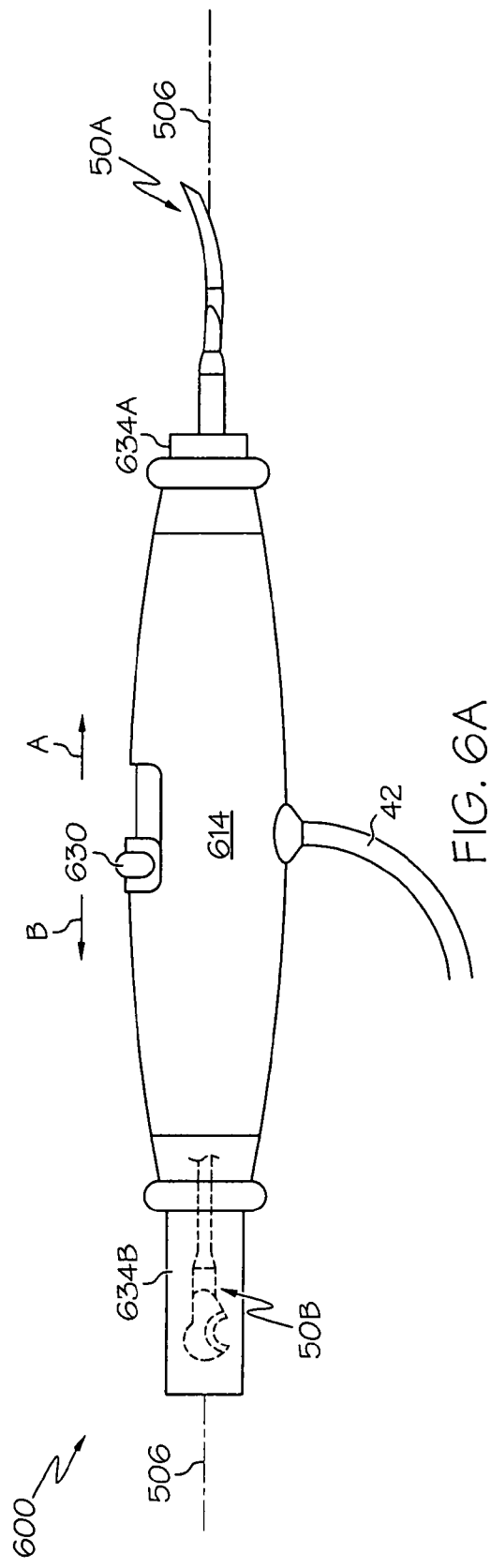
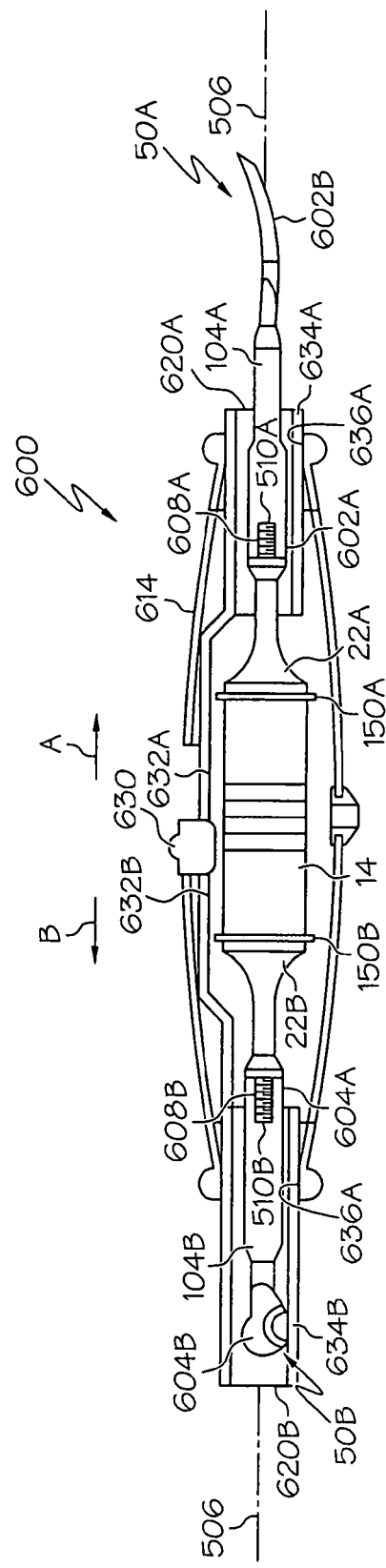
FIG. 6A
FIG. 6B

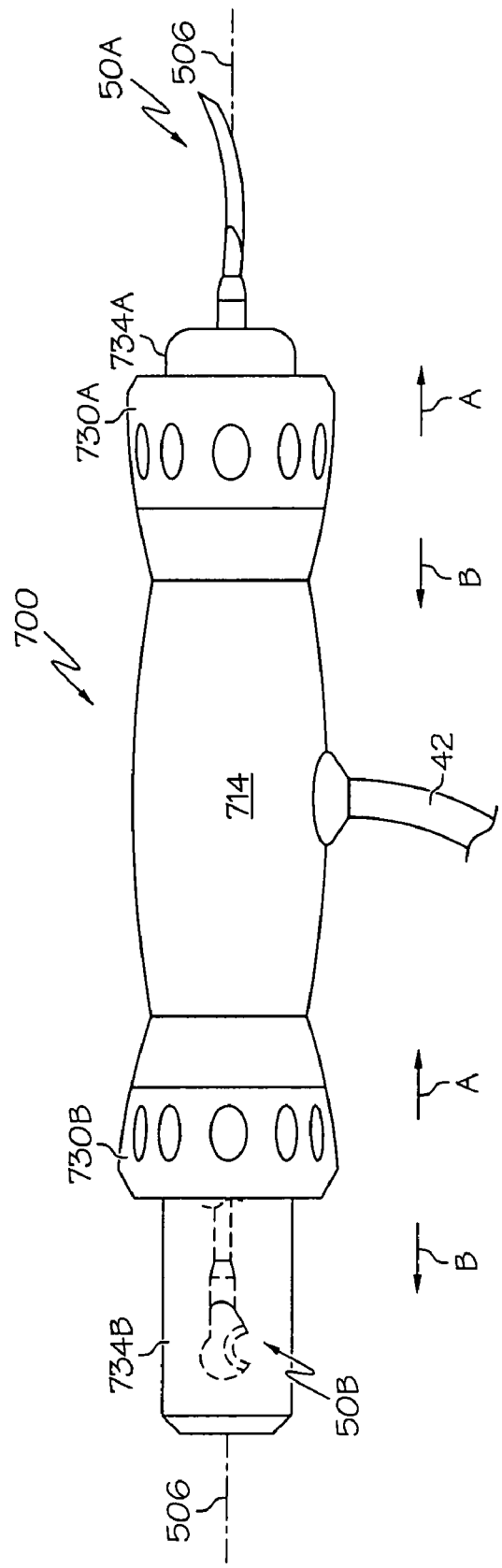
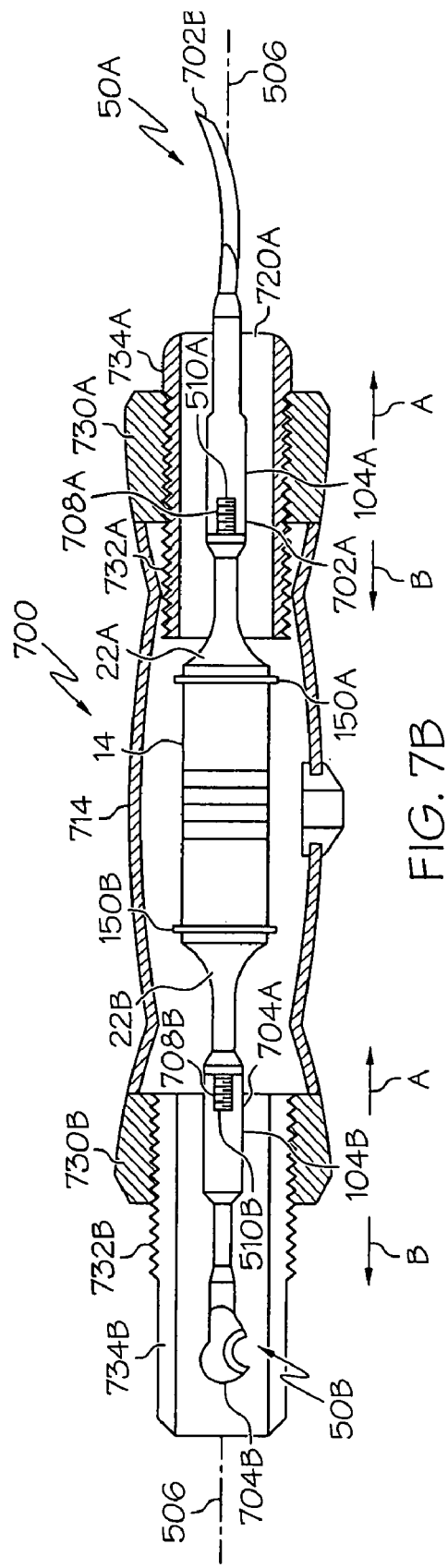
FIG. 7A
FIG. 7B

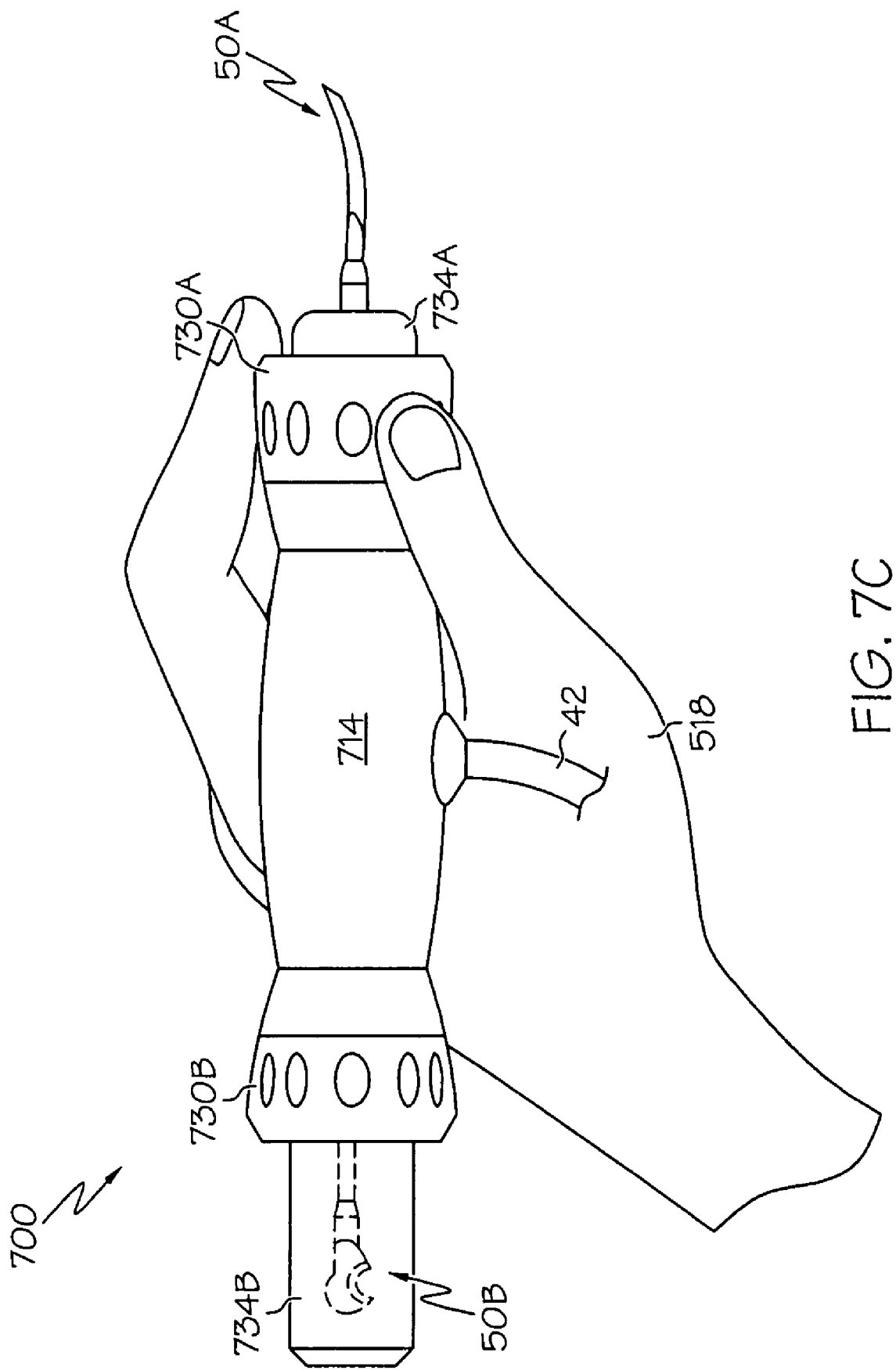

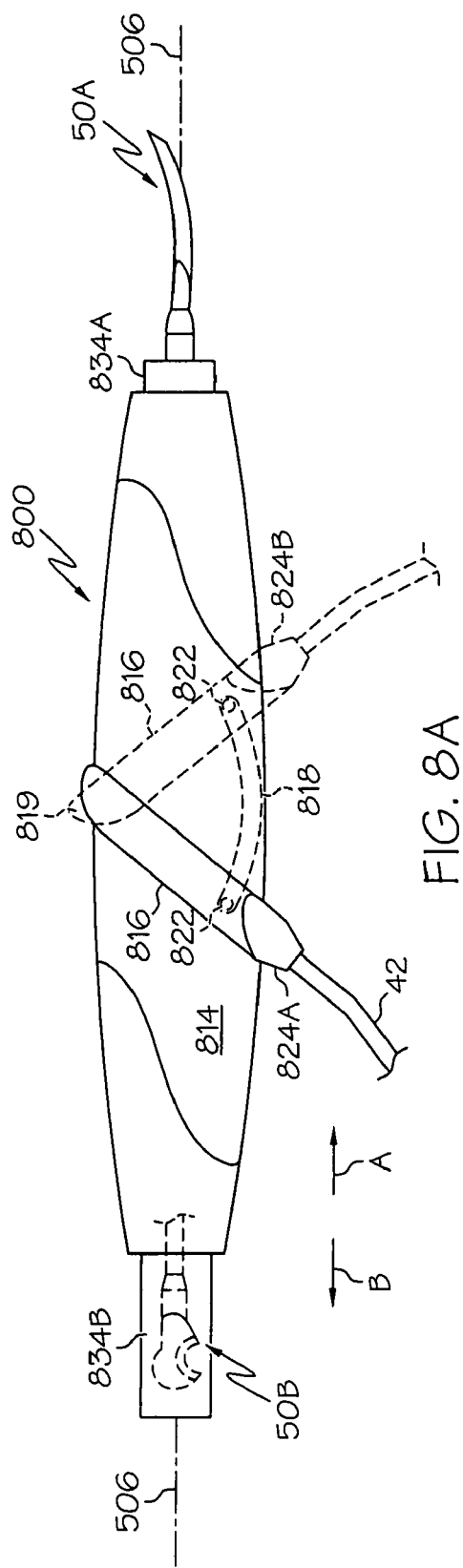
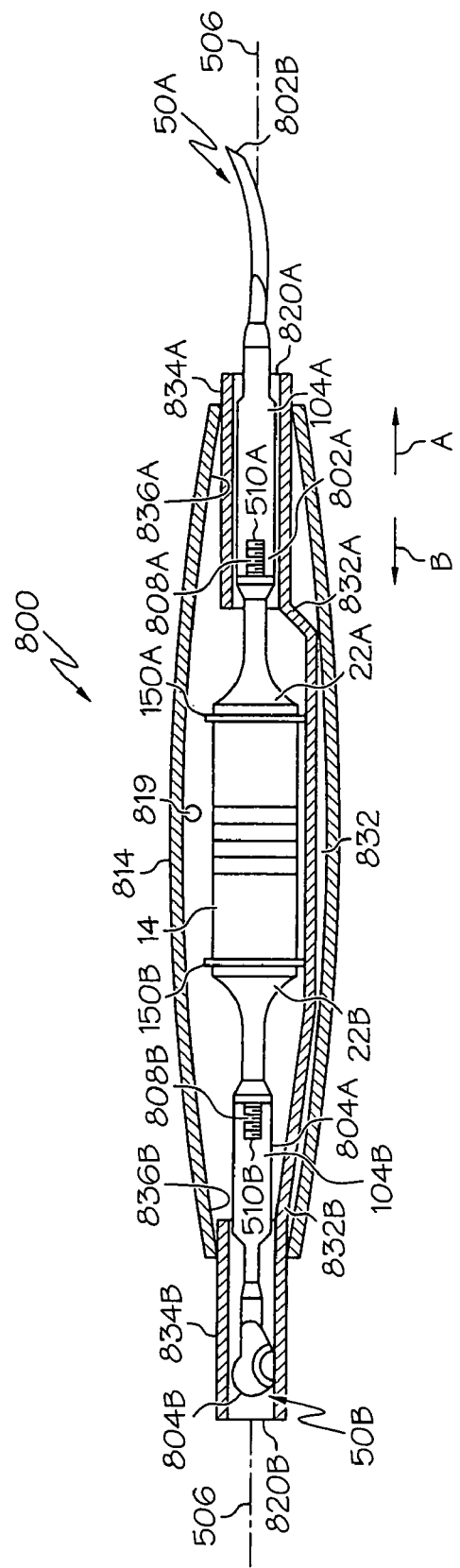
FIG. 8A
FIG. 8B

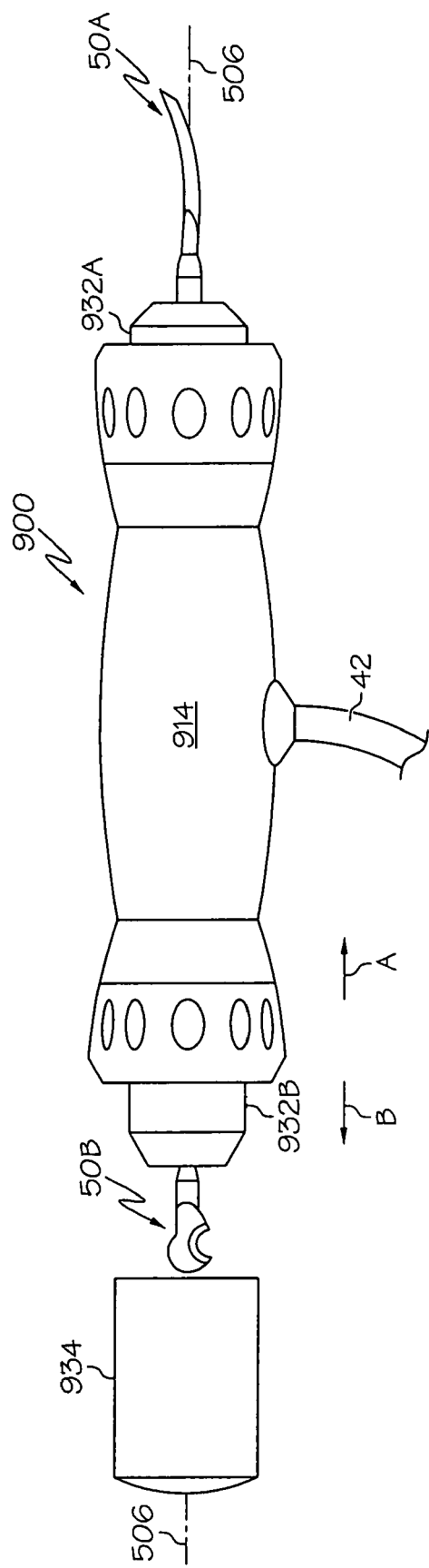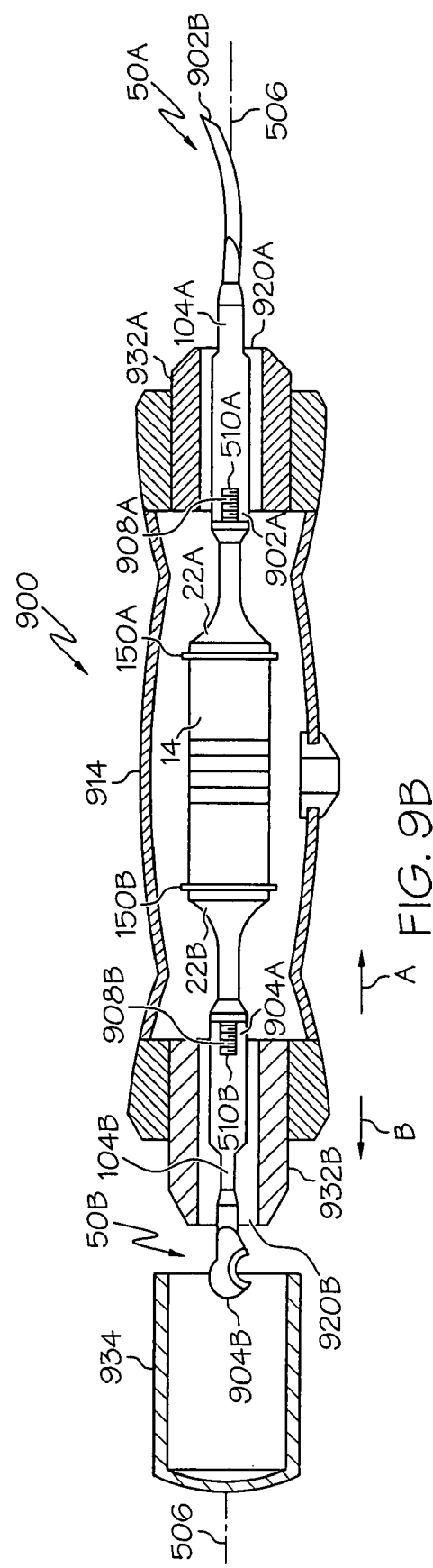

MULTIPLE END EFFECTORS ULTRASONIC SURGICAL INSTRUMENTS

BACKGROUND

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, elevate, or coagulate tissue or separate muscle tissue from bone. Ultrasonic instruments utilizing solid core technology are particularly advantageous because of the amount of ultrasonic energy that may be transmitted from the ultrasonic transducer, through a waveguide, to the surgical end effector. Such instruments may be used for open procedures or minimally invasive procedures, such as endoscopic or laparoscopic procedures, wherein the end effector is passed through a trocar to reach the surgical site.

Activating or exciting the end effector of such instruments at ultrasonic frequencies induces longitudinal, transverse, or torsional vibratory movement that generates localized heat within adjacent tissue, facilitating both cutting and coagulating. Because of the nature of ultrasonic instruments, a particular ultrasonically actuated end effector may be designed to perform numerous functions, including, for example, cutting, clamping, and coagulating.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end effector via an ultrasonic waveguide extending from the transducer section to the surgical end effector. The waveguides and end effectors are most preferably designed to resonate at the same frequency as the transducer. Therefore, when an end effector is attached to a transducer the overall system frequency is the same frequency as the transducer itself.

The zero-to-peak amplitude of the longitudinal ultrasonic vibration at the tip, d, of the end effector behaves as a simple sinusoid at the resonant frequency as given by:

$$d = A \sin(\omega t)$$

where:
$\omega$=the radian frequency which equals $2\pi$ times the cyclic frequency, f; and
A=the zero-to-peak amplitude.
The longitudinal excursion is defined as the peak-to-peak (p-t-p) amplitude, which is just twice the amplitude of the sine wave or 2 A.

Solid core ultrasonic surgical instruments may be divided into two types, single element end effector devices and multiple-element end effector. Single element end effector devices include instruments such as scalpels, and ball coagulators. Single-element end effector instruments have limited ability to apply blade-to-tissue pressure when the tissue is soft and loosely supported. Substantial pressure may be necessary to effectively couple ultrasonic energy to the tissue. This inability to grasp the tissue results in a further inability to fully coapt tissue surfaces while applying ultrasonic energy, leading to less-than-desired hemostasis and tissue joining. The use of multiple-element end effectors such as clamping coagulators includes a mechanism to press tissue against an ultrasonic blade that can overcome these deficiencies.

Ultrasonic clamp coagulators provide an improved ultrasonic surgical instrument for cutting/coagulating tissue, particularly loose and unsupported tissue, wherein the ultrasonic blade is employed in conjunction with a clamp for applying a compressive or biasing force to the tissue, to achieve faster coagulation and cutting of the tissue.

It may be desirable to provide an ultrasonic instrument comprising a readily selectively deployable ultrasonically actuatable end effectors, such as readily selectively deployable actuatable ultrasonic blades and/or clamp coagulators. It may be desirable to provide an ultrasonic instrument comprising easily and quickly exchangeable end effectors suitable for performing fine and delicate surgeries. In performing such fine surgeries, it may be desirable to easily and quickly exchange between various ultrasonically actuatable end effectors.

SUMMARY

In one embodiment a surgical instrument comprises a transducer configured to produce vibrations along a longitudinal axis at a predetermined frequency. The transducer comprises a first end and a second end. A first resonator portion comprises a first end coupled to the first end of the transducer. The first resonator comprises a second end adapted to receive a first ultrasonic transmission waveguide. A second resonator portion comprises a first end coupled to the second end of the transducer. The second resonator comprises a second end adapted to receive a second ultrasonic transmission waveguide.

FIGURES

The novel features of the various embodiments are set forth with particularity in the appended claims. The various embodiments, however, both as to organization and methods of operation, together with further objects and advantages thereof, may best be understood by reference to the following description, taken in conjunction with the accompanying drawings as follows.

FIG. 1 illustrates one embodiment of an ultrasonic system.

Figure 5C:
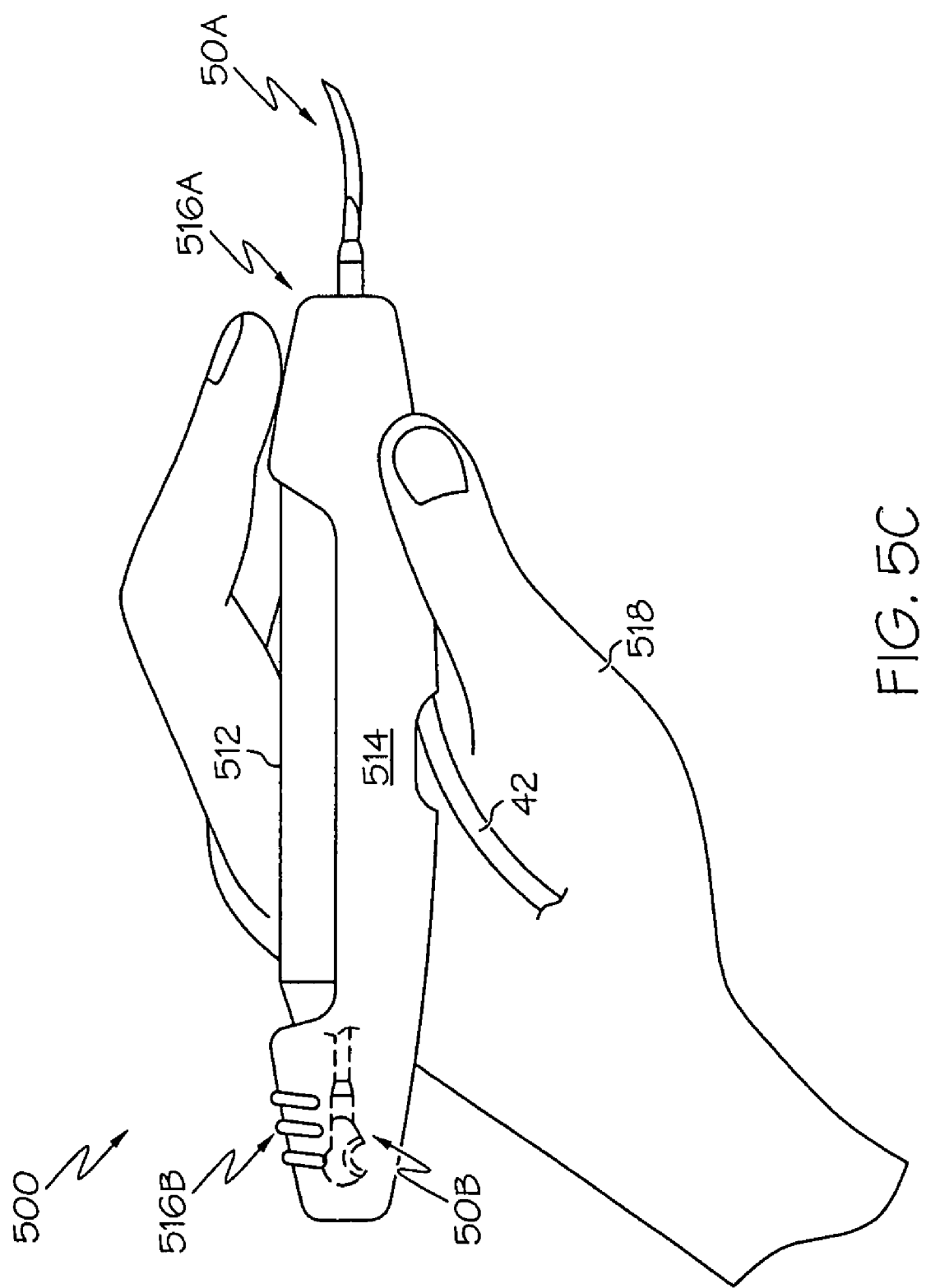

FIGS. 5A, 5B, and 5C illustrate one embodiment of an ultrasonic instrument.

Figure 6C:
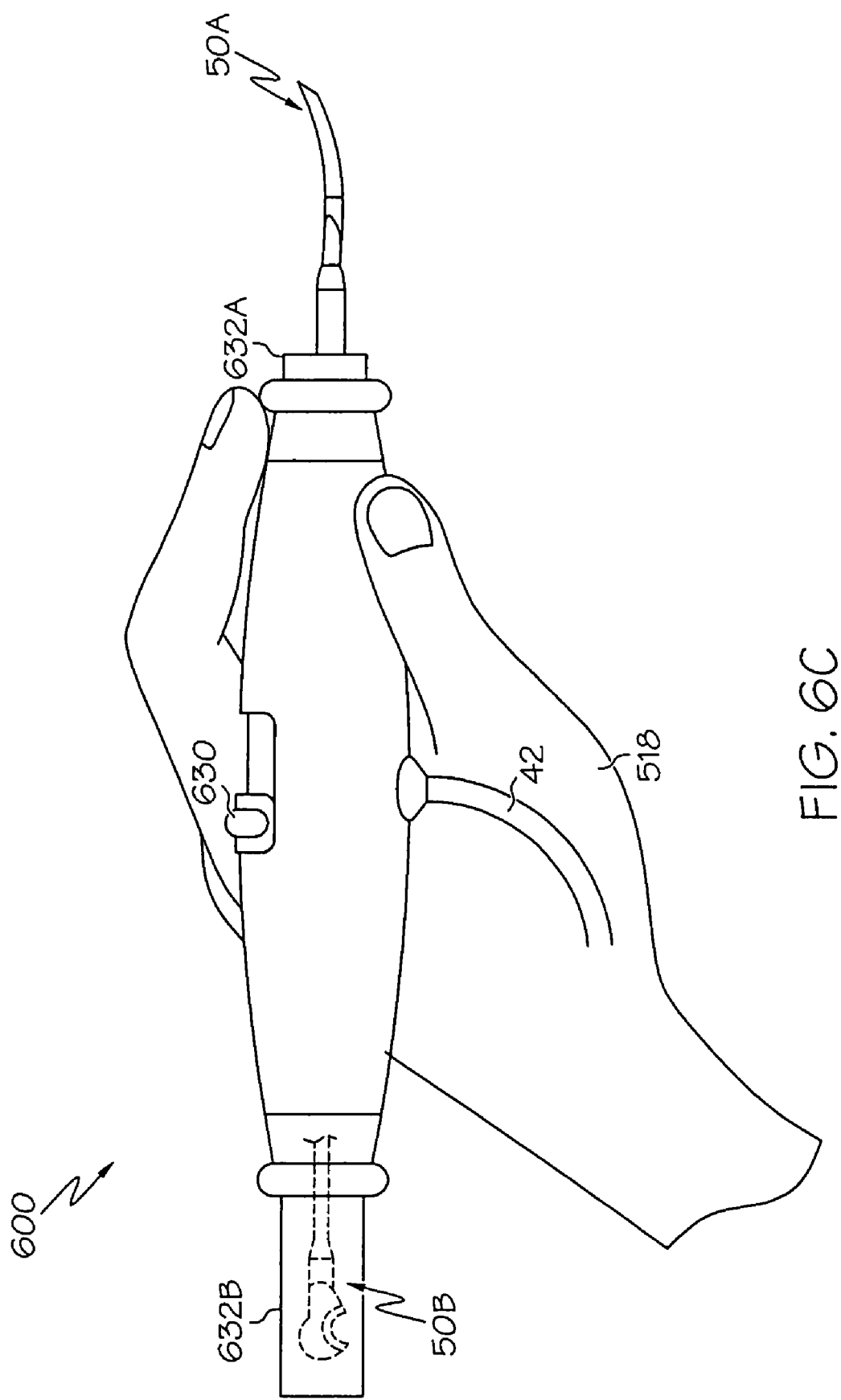

FIGS. 6A, 6B, and 6C illustrate one embodiment of an ultrasonic instrument.

FIGS. 7A, 7B, and 7C illustrate one embodiment of an ultrasonic instrument.

Figure 8C:
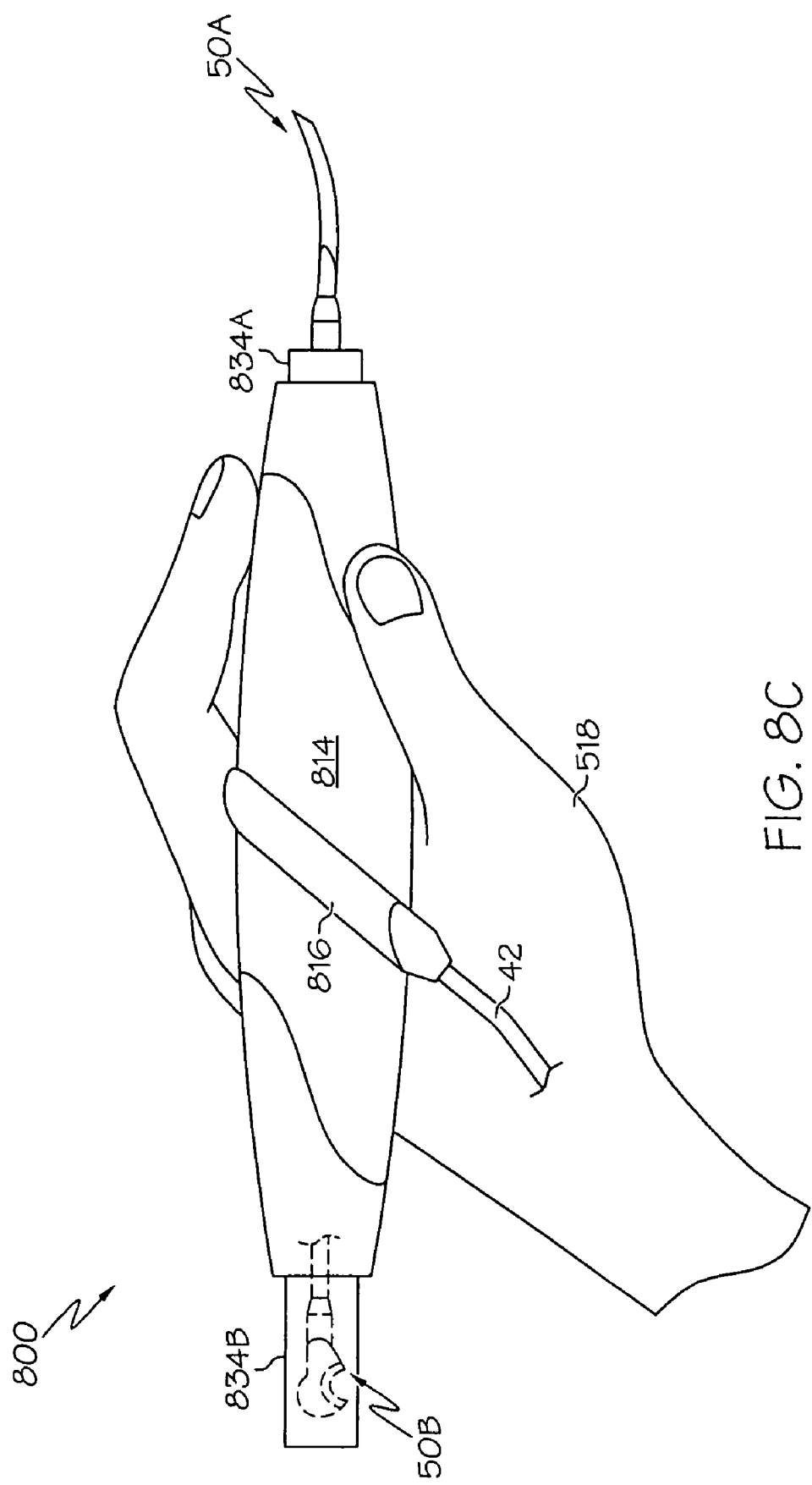

FIGS. 8A, 8B, and 8C illustrate one embodiment of an ultrasonic instrument.

Figure 9C:
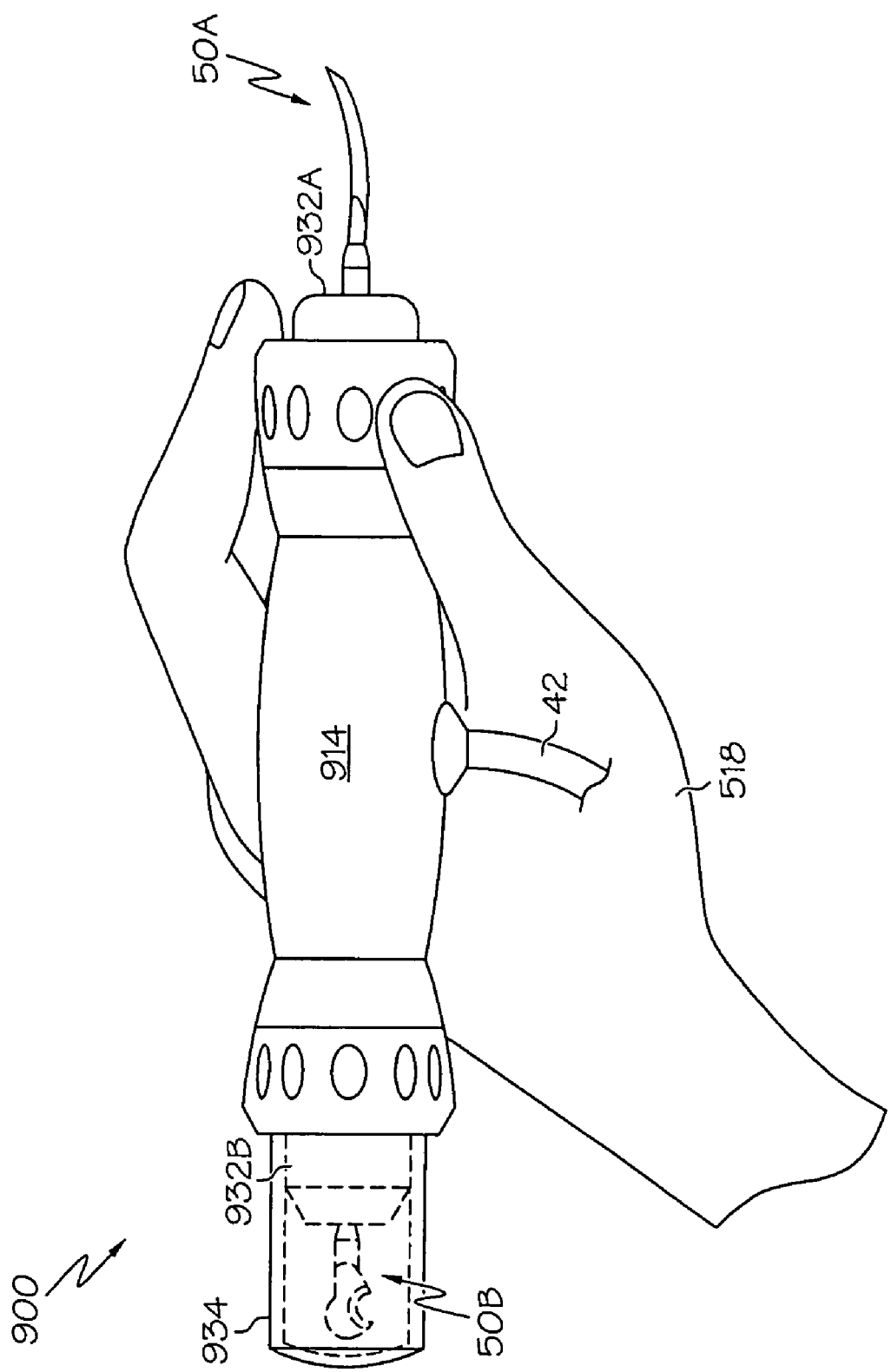

FIGS. 9A, 9B, and 9C illustrate one embodiment of an ultrasonic instrument.

DESCRIPTION

Before explaining the various embodiments in detail, it should be noted that the embodiments are not limited in their application or use to the details of construction and arrangement of parts illustrated in the accompanying drawings and description. The illustrative embodiments may be implemented or incorporated in other embodiments, variations and modifications, and may be practiced or carried out in various ways. For example, the surgical instruments and blade configurations disclosed below are illustrative only and not meant to limit the scope or application thereof. Furthermore, unless otherwise indicated, the terms and expressions employed herein have been chosen for the purpose of describing the illustrative embodiments for the convenience of the reader and are not to limit the scope thereof.

The various embodiments relate, in general, to ultrasonic surgical instruments and, more particularly, to an ultrasonic surgical instruments comprising multiple end effectors. Furthermore, the various embodiments relate, in general, to ultrasonic surgical instruments that provide a quick exchange between the multiple end effectors.

Examples of ultrasonic surgical instruments are disclosed in U.S. Pat. Nos. 5,322,055 and 5,954,736 and in combination with ultrasonic blades and surgical instruments disclosed in U.S. Pat. Nos. 6,309,400 B2, 6,278,218B1, 6,283,981 B1, and 6,325,811 B1, for example, are incorporated herein by reference in their entirety. These references disclose ultrasonic surgical instrument design and blade designs where a longitudinal mode of the blade is excited. Because of asymmetry or asymmetries, these blades exhibit transverse and/or torsional motion where the characteristic "wavelength" of this non-longitudinal motion is less than that of the general longitudinal motion of the blade and its extender portion. Therefore, the wave shape of the non-longitudinal motion will present nodal positions of transverse/torsional motion along the tissue effector while the net motion of the active blade along its tissue effector is non-zero (i.e. will have at least longitudinal motion along the length extending from its distal end, an antinode of longitudinal motion, to the first nodal position of longitudinal motion that is proximal to the tissue effector portion).

Various embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined with the features of other embodiments. Such modifications and variations are intended to be included within the scope of the claims.

In one embodiment, an ultrasonic surgical instrument comprises a transducer configured to produce vibrations at a predetermined frequency. The transducer comprises first and second ends and is configured to produce vibrations along a longitudinal axis at a predetermined frequency. A first selectively deployable ultrasonically actuatable end effector extends along the longitudinal axis in a first direction and is coupled to the first end of the transducer. A second selectively deployable ultrasonically actuatable end effector extends along the longitudinal axis in an opposite direction and is coupled to the second end of the transducer. The first and second ultrasonic end effectors each include a body having a proximal end and a distal end. The distal end is movable substantially relative to the longitudinal axis by the vibrations produced by the transducer. In one embodiment, the ultrasonic instrument comprises selectable ultrasonically actuatable end effectors. The ultrasonic instrument can be held by a clinician and may be employed in fine and delicate surgeries. During such fine surgeries, it may be desirable to quickly exchange between various ultrasonically actuatable end effectors.

The term "end effector" comprises any ultrasonically actuatable instrument having on end adapted to couple to one end of an ultrasonic transmission waveguide and having another end suitable to cut, dissect, clamp, or coagulate tissue using energy in the form of mechanical vibrations transmitted thereto at ultrasonic frequencies. End effectors may comprise ultrasonic surgical blades comprising cutting and/or coagulating edges. End effectors also may comprise clamping devices to hold organic tissue to assist cutting and coagulating. The end effectors may be rotatable, articulatable, pivotable, actuatable, or otherwise controllable by the clinician. The end effectors may be particularly suited for use in minimally invasive procedures, such as endoscopic or laparoscopic procedures, wherein the end effector is passed through a trocar to reach the surgical site. The embodiments, however, are not limited in this context.

In one embodiment, an ultrasonic surgical instrument comprises a transducer configured to produce vibrations along a longitudinal axis at a predetermined ultrasonic frequency. The transducer comprises first and second ends adapted to ultrasonically couple to respective first and second ultrasonic transmission waveguides. The first ultrasonic transmission waveguide is coupled to the first end of the transducer and extends substantially along the longitudinal axis in one direction. The second ultrasonic transmission waveguide is coupled to the second end of the transducer and extends substantially along the longitudinal axis in an opposite direction from the first ultrasonic transmission waveguide. The first and second ultrasonic transmission waveguides may be configured to receive selectively deployable ultrasonically actuatable end effectors, wherein the distal end of the end effector is displaced relative to the longitudinal axis by the mechanical vibrations produced by the transducer and transmitted to the end effector at ultrasonic frequencies.

In one embodiment, a surgical instrument comprises a transducer adapted to couple to at least two active ultrasonic transmission waveguides (e.g., horns) and mounting stud arrangements to enable mounting and simultaneously vibrating the first and second selectively deployable ultrasonically actuatable end effectors at ultrasonic frequencies. Generally, one end effector may be selected and employed at a given time. In one embodiment, the selectively deployable ultrasonically actuatable end effectors may comprise relatively compact form factors suitable for use fine and delicate surgeries. The selectively deployable ultrasonically actuatable end effector that is employed in a procedure is referred to the active end effector. The selectively deployable ultrasonically actuatable end effector that is not employed in the procedure is referred to as the non-deployed end effector. The non-deployed end effector consumes minimal power, generates minimal or no heat, and may be stowed or shrouded substantially within the surgical instrument and/or a protective cover so as not to interfere with the procedure and/or contact unwanted objects. In other embodiments, the operation of the surgical instrument in general may be electrically inhibited when both end effectors are exposed outside of the surgical instrument and/or the protective cover. This may occur in transitional phases when selecting either one of the end effectors. Note that end effectors to be used in various embodiments can be designed by those skilled in the art to consume minimal quiescent ultrasonic power, and thereby generate minimal heat. Design of such end effectors involves selection of adequate end effector mechanical gain, overall mass, length, and proper material. Furthermore, the non-deployed end effector consumes minimal quiescent ultrasonic power also due to the fact that it is not loaded by tissue, thereby generating substantially low quiescent heat due to loading.

As described and illustrated herein, the surgical instrument may comprise a housing adapted to contain the ultrasonic transducer and the first and second ultrasonic transmission waveguides to allow one-handed operation by the clinician. Various embodiments of the surgical instruments described and illustrated herein employ ultrasonic technology, provide selectively deployable ultrasonically actuatable end effectors that may be exchanged quickly and easily during a surgical procedure by the clinician, and provide end effectors with form factors suitable for fine and delicate surgical procedures. The embodiments, however, are not limited in this context.

FIG. 1 illustrates one embodiment of an ultrasonic system 10. One embodiment of the ultrasonic system 10 comprises an ultrasonic signal generator 12 coupled to an ultrasonic transducer 14, a hand piece assembly 60 comprising a hand piece housing 16, a first selectively deployable end effector 50A, and a second selectively deployable end effector 50B. The ultrasonic transducer 14, which is known as a "Langevin stack", generally includes a transduction portion 18, a first resonator portion 22A, and a second resonator portion 22B, and ancillary components. The first or second resonator portions 22A, B may be referred to as a bell or a horn. The transduction portion 18 comprises a first end 33A and a second end 33B. The total construction is a resonator. The ultrasonic transducer 14 has a length in the longitudinal direction that is preferably an integral number of one-half wavelengths ($n\lambda/2$) as described in more detail herein. A first acoustic assembly 24A includes the ultrasonic transducer 14, an adapter 26A, a velocity transformer 28A, and a surface 30A. A second acoustic assembly 24B includes the ultrasonic transducer 14, an adapter 26B, a velocity transformer 28B, and a surface 30B.

It will be appreciated that the terms "proximal" and "distal" are used herein with reference to the transduction portion 18 and with reference to a clinician gripping the hand piece assembly 60 during use. The hand piece assembly 60 comprises first and second ends 55A, B relative to the transduction portion 18. During use or while the first end effector 50A is active, it is distal with respect to the more proximal transduction portion 18. During use or while the second end effector 50B is active, it is distal with respect to the more proximal transduction portion 18. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The first resonator portion 22A comprises a first end connected to the first end 33A of the transduction portion 18 and a second end to couple to longitudinally projecting proximal end 54A of an ultrasonic transmission waveguide 104A. The second resonator portion 22B comprises a first end connected the second end 33B of the transduction portion 18 and a second end to couple to longitudinally projecting proximal ends 54B of an ultrasonic transmission waveguide 104B. The length of the first resonator portion 22A and the second resonator portion 22B may be determined by a number of variables, including the thickness of the transduction portion 18, the density and modulus of elasticity of the material used to manufacture the first and second resonator portions 22A, B, and the resonant frequency of the ultrasonic transducer 14. The first and second resonator portions 22A, B may be tapered inwardly from the first ends to the respective second ends. The tapered geometry acts to amplify the ultrasonic vibration amplitude as the respective velocity transformers 28A, B, may have no amplification. A suitable vibrational frequency range may be about 20 Hz to 120 kHz and a well-suited vibrational frequency range may be about 30-100 kHz and one example operational vibrational frequency may be approximately 55.5 kHz. The first and second resonator portions 22A, B are preferably fabricated from titanium, aluminum, stainless steel, or any other suitable material.

Piezoelectric elements 32 may be fabricated from any suitable material, such as, for example, lead zirconate-titanate, lead meta-niobate, lead titanate, barium titanate, or other piezoelectric ceramic materials. Each of positive electrodes 34, negative electrodes 36, and the piezoelectric elements 32 comprise a bore extending through the center. The positive and negative electrodes 34 and 36 are electrically coupled to wires 38 and 40 (not shown in FIG. 1 but shown in FIG. 4), respectively. The wires 38 and 40 are encased within a cable 42 (FIG. 4) and electrically connectable to the ultrasonic signal generator 12 of the ultrasonic system 10.

The ultrasonic transducer 14 coupled to the first acoustic assembly 24A converts electrical signals from the ultrasonic signal generator 12 into mechanical energy that results in primarily longitudinal vibratory motion of the first acoustic assembly 24A and the first end effector 50A at ultrasonic frequencies. Similarly, the ultrasonic transducer 14 coupled to the second acoustic assembly 24B converts electrical signals from the ultrasonic signal generator 12 into mechanical energy that results in primarily longitudinal vibratory motion of the second acoustic assembly 2BA and the second end effector 50B at ultrasonic frequencies. Suitable generators are available as model number GEN04, from Ethicon Endo-Surgery, Inc., Cincinnati, Ohio. When the acoustic assembly 24 is energized, a vibratory motion standing wave is generated through the first and second acoustic assemblies 24A, B. The amplitude of the vibratory motion at any point along the first and second acoustic assemblies 24A, B depends on the location along the first and second acoustic assemblies 24A, B at which the vibratory motion is measured. A minimum or zero crossing in the vibratory motion standing wave is generally referred to as a node (i.e., where motion is minimal), and a local absolute value maximum or peak in the standing wave is generally referred to as an anti-node (i.e., where local motion is maximal). The distance between an anti-node and its nearest node is one-quarter wavelength ($\lambda/4$).

The wires 38 and 40 (FIG. 4) transmit an electrical signal from the ultrasonic signal generator 12 to the positive electrodes 34 and the negative electrodes 36. The piezoelectric elements 32 are energized by the electrical signals supplied from the ultrasonic signal generator 12 in response to an activation switch such as a foot switch 44 to produce an acoustic standing wave in the first and second acoustic assemblies 24A, B. The electrical signal causes disturbances in the piezoelectric elements 32 in the form of repeated small displacements resulting in large alternating compression and tension forces within the material. The repeated small displacements cause the piezoelectric elements 32 to expand and contract in a continuous manner along the axis of the voltage gradient, producing longitudinal waves of ultrasonic energy. The ultrasonic energy is transmitted through the acoustic assemblies 24A, B to the end effector 50 via respective ultrasonic transmission waveguides 104A, B.

For the acoustic assemblies 24A, B to deliver energy to the respective first and second end effectors 50A, B, all components of the acoustic assemblies 24A, B must be acoustically coupled to the respective end effectors 50A, B. The first end of the ultrasonic transducer 14 may be acoustically coupled at the surface 30A to a first proximal end of the ultrasonic transmission waveguide 104A by a threaded connection such as a stud 48A. Similarly, the second end 33B of the ultrasonic transducer 14 may be acoustically coupled at the surface 30B to a second end of the ultrasonic transmission waveguide 104B by a threaded connection such as a stud 48B.

The components of each of the acoustic assemblies 24A, B may be acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of each of the acoustic assemblies 24A, B, and where n is any positive integer. It is also contemplated that the acoustic assemblies 24A, B may incorporate any suitable arrangement of acoustic elements.

The length of each of the first and second selectively deployable ultrasonically actuatable end effectors 50A, B may be substantially equal to an integral multiple of one-half wavelengths ($n\lambda/2$). Respective ends 52A, B of the end effectors 50A, B may be disposed near an antinode in order to provide the maximum longitudinal excursion of the end 52A or 52B when in use. It will be appreciated that either one of the respective ends 52A, B may be referred to as distal ends with reference to a clinician gripping the hand piece assembly 60 during use. When the transducer assembly is energized, the distal ends 52A, B of the respective end effectors 50A, B may be configured to move in the range of approximately 10 to 500 microns peak-to-peak, and preferably in the range of about 30 to 150 microns at a predetermined vibrational frequency of 55.5 kHz, for example.

The selectively deployable ultrasonically actuatable end effectors 50A, B may be coupled to the respective ultrasonic transmission waveguides 104A, B. The end effectors 50A, B and the respective ultrasonic transmission waveguides 104A, B may be formed as a single unit construction (as illustrated) from a material suitable for transmission of ultrasonic energy such as, for example, Ti6Al4V (an alloy of titanium including aluminum and vanadium), aluminum, stainless steel, or other known materials. Alternately, the ultrasonic end effectors 50A, B may be separable (and of differing composition) from the respective ultrasonic transmission waveguides 104A, B, and coupled by, for example, a stud, weld, glue, quick connect, or other suitable techniques. The length of the ultrasonic transmission waveguides 104A, B may be an integral number of one-half wavelengths ($n\lambda/2$), for example. The ultrasonic transmission waveguides 104A, B may be fabricated from a solid core shaft constructed out of material that propagates ultrasonic energy efficiently, such as a titanium alloy (i.e., Ti6Al4V) or an aluminum alloy, for example. The ultrasonic transmission waveguides 104A, B also may be fabricated from a hollow core shaft constructed out of similar materials. The ultrasonic transmission waveguides 104A, B also may be fabricated with a combination solid/hollow core shaft, for example, a solid core shaft with hollow cavities positioned at various locations along the length of the shaft.

The ultrasonic transmission waveguides 104A, B each comprise respective longitudinally projecting proximal ends 54A, B at a first end to couple to the respective surfaces 30A, B. In the illustrated embodiment, the longitudinally projecting proximal ends 54A, B of the ultrasonic transmission waveguides 104A, B are coupled to the respective surfaces 30A, B by a threaded connection such as the studs 48A, B, respectively. Other coupling techniques such as a weld, glue, quick connect, or other suitable techniques, may be employed. In the embodiment illustrated in FIG. 1, each of the ultrasonic transmission waveguides 104A, B includes a plurality of stabilizing silicone rings or compliant supports 56A, B positioned at a plurality of nodes. The silicone rings 56A, B dampen undesirable vibration and isolate the ultrasonic energy from removable sheaths 58A, B assuring the flow of ultrasonic energy in a longitudinal direction to the respective ends 52A, B of the respective end effectors 50A, B with maximum efficiency.

As shown in FIG. 1, the outer sheaths 58A, B protect the user and the patient from the ultrasonic vibrations produced by the respective ultrasonic transmission waveguides 104A, B. The outer sheaths 58A, B generally include respective hubs 62A, B and respective elongated tubular members 64A, B. The tubular members 64A, B are attached to the respective hubs 62A, B and have openings extending longitudinally therethrough. The outer sheaths 58A, B are threaded onto the respective distal ends 55A, B of the housing 16. The ultrasonic transmission waveguides 104A, B extend through the opening of the respective tubular members 64A, B and the silicone rings 56A, B isolate the ultrasonic transmission waveguides 104A, B from the outer sheaths 58. The outer sheaths 58A, B are attached to the ultrasonic transmission waveguides 104A, B with respective isolator pins 112A, B. The hole in the ultrasonic transmission waveguides 104A, B may be located nominally near a displacement node. The ultrasonic transmission waveguides 104A, B are threaded onto the hand piece assembly 60 by the respective studs 48A, B. The flat portions formed on the hubs 62A, B allow the hand piece assembly 60 to be torqued to a required level.

The hubs 62A, B of the sheath 58 is preferably constructed from plastic, and the tubular member 64 may be fabricated from stainless steel. Alternatively, the ultrasonic transmission waveguides 104A, B may be isolated from outside contact by a polymeric material formed thereon.

The second ends of the ultrasonic transmission waveguides 104A, B may be coupled to the first ends of the respective end effectors 50A, B by internal threaded connections, preferably at or near an antinode. It is contemplated that the end effectors 50A, B may be attached to the respective ultrasonic transmission waveguides 104A, B by any suitable means, such as a welded joint or the like. Although the end effectors 50A, B may be detachable from the ultrasonic transmission waveguides 104A, B, it is also contemplated that the end effectors 50A, B and the respective ultrasonic transmission waveguides 104A, B may be formed as a single unitary pieces.

Figure 2A:
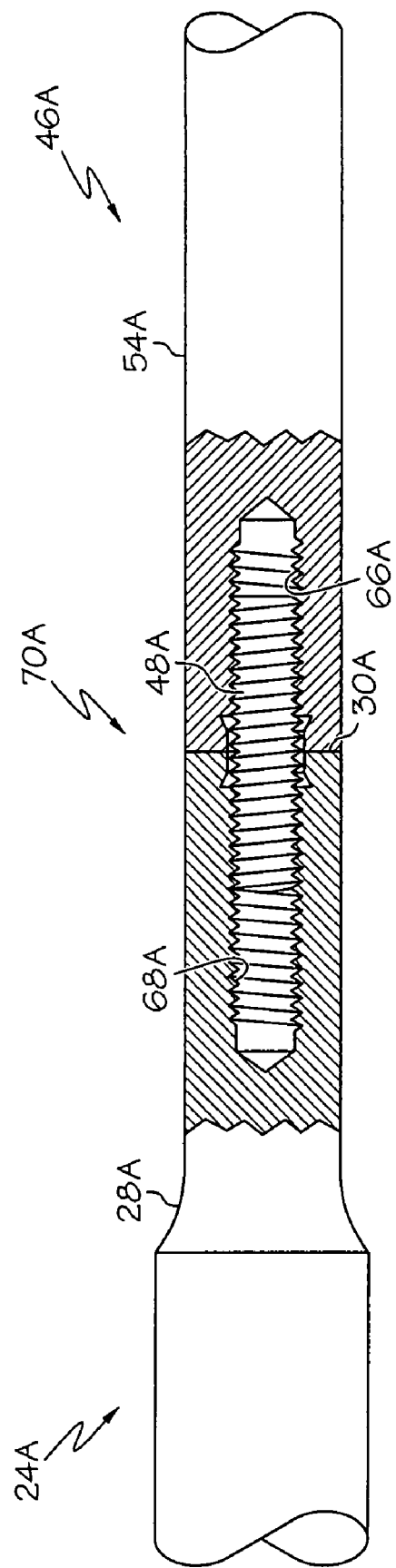
FIG. 2A illustrates one embodiment of a connection union/joint for an ultrasonic instrument.

FIG. 2A illustrates one embodiment of a connection union/joint 70A for an ultrasonic instrument. In one embodiment, the connection union/joint 70A may be formed between the longitudinally projecting proximal end 54A of the ultrasonic transmission waveguide 104A and the surface 30A of the velocity transformer 28A at the distal end of the acoustic assembly 24A. A first end of the longitudinally projecting proximal end 54A comprises a female threaded substantially cylindrical recess 66A to receive a portion of the threaded stud 48A therein. A second end of the velocity transformer 28A also may comprise a female threaded substantially cylindrical recess 68A to receive a portion of the threaded stud 40A. The recesses 66A, 68A are substantially circumferentially and longitudinally aligned.

Figure 2B:
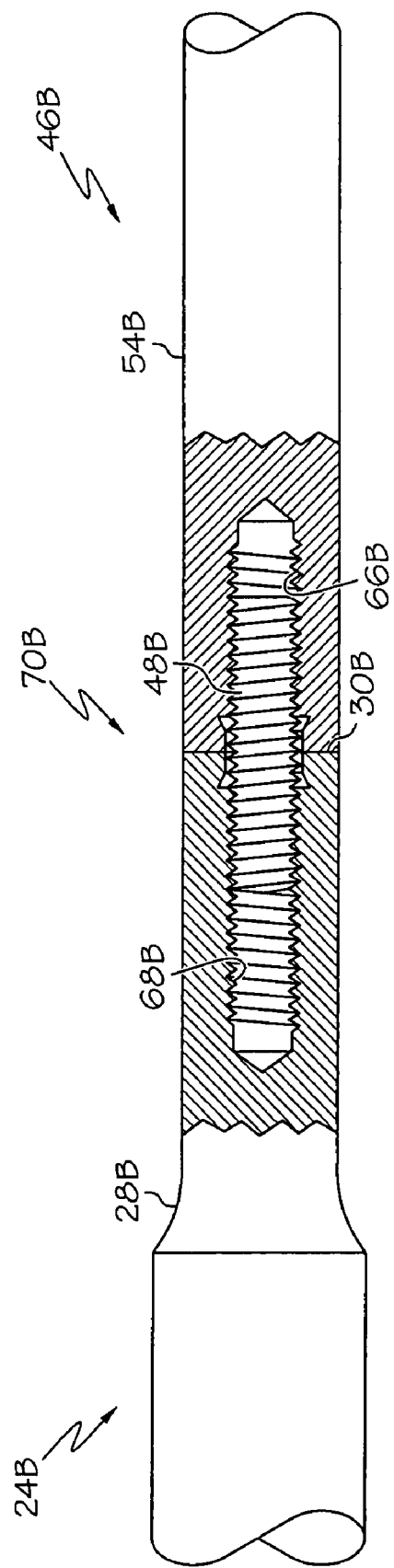
FIG. 2B illustrates one embodiment of a connection union/joint for an ultrasonic instrument.

FIG. 2B illustrates one embodiment of a connection union/joint 70B for an ultrasonic instrument. In one embodiment, the connection union/joint 70B may be formed between the longitudinally projecting proximal end 54B of the ultrasonic transmission waveguide 104B and the surface 30B of the velocity transformer 28B at the distal end of the acoustic assembly 24B. A first end of the longitudinally projecting proximal end 54B comprises a female threaded substantially cylindrical recess 66B to receive a portion of the threaded stud 48B therein. A second end of the velocity transformer 28B also may comprise a female threaded substantially cylindrical recess 68B to receive a portion of the threaded stud 40A. The recesses 66B, 68B are substantially circumferentially and longitudinally aligned.

Figure 3A:
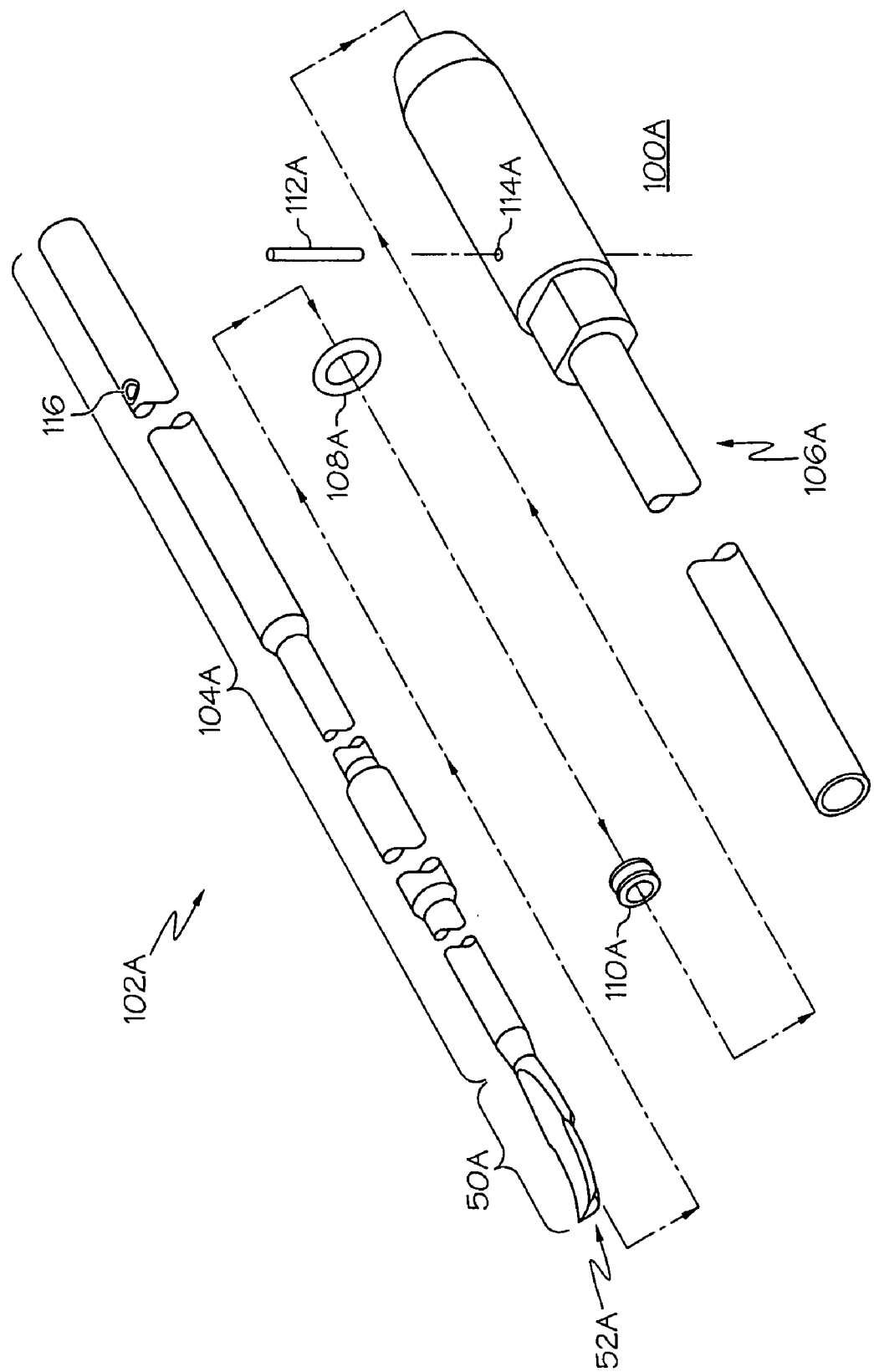
FIG. 3A illustrates one embodiment of an ultrasonic transmission waveguide positioned in an outer sheath by a mounting O-ring and a sealing ring.
Figure 3B:
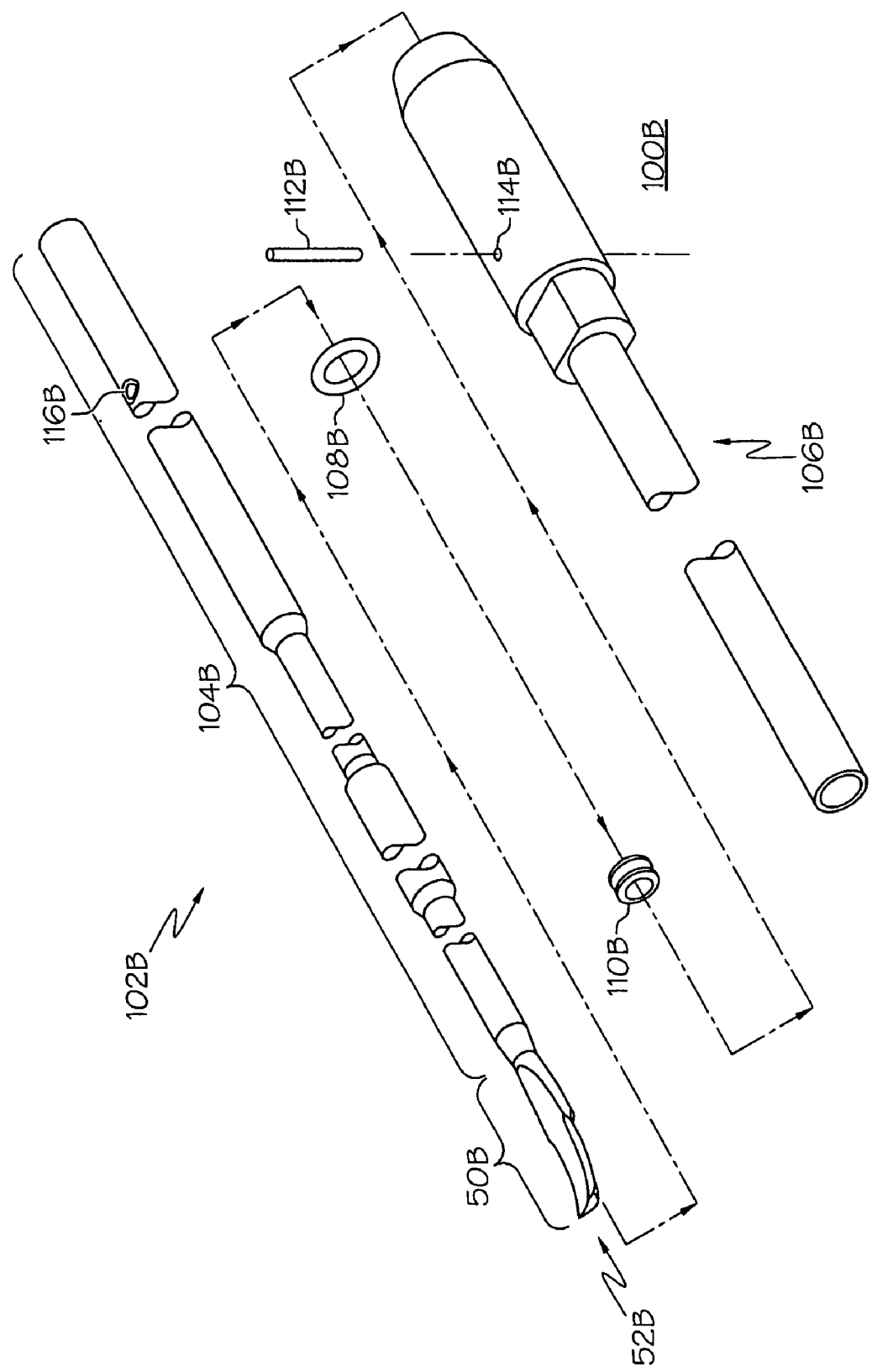
FIG. 3B illustrates one embodiment of an ultrasonic transmission waveguide positioned in an outer sheath by a mounting O-ring and a sealing ring.

FIGS. 3A and 3B illustrate exploded perspective views of one embodiment of sterile ultrasonic surgical instruments 100A, B. The ultrasonic surgical instruments 100A, B may be employed with the above-described ultrasonic system 10. However, as described herein, those of ordinary skill in the art will understand that the various embodiments of the ultrasonic surgical instruments disclosed herein as well as any equivalent structures thereof could conceivably be effectively used in connection with other known ultrasonic surgical instruments without departing from the scope thereof. Thus, the protection afforded to the various ultrasonic surgical blade embodiments disclosed herein should not be limited to use only in connection with the embodiments of the ultrasonic surgical instrument described above.

The ultrasonic surgical instruments 100A, B may be sterilized by methods known in the art such as, for example, gamma radiation sterilization, ethylene oxide processes, autoclaving, soaking in sterilization liquid, or other known processes. In the illustrated embodiments, ultrasonic transmission assemblies 102A, B include an ultrasonic end effector, the generally designated respective ultrasonic end effectors 50A, B, and the respective ultrasonic transmission waveguides 104A B. The ultrasonic end effectors 50A, B and the respective ultrasonic transmission waveguides 104A, B are illustrated as a single unit construction from a material suitable for transmission of ultrasonic energy such as, for example, Ti6Al4V (an alloy of titanium including aluminum and vanadium), aluminum, stainless steel, or other known materials. Alternately, the ultrasonic end effectors 50A, B may be separable (and of differing composition) from the respective ultrasonic transmission waveguides 104A, B, and coupled by, for example, a stud, weld, glue, quick connect, or other known methods. The length of the ultrasonic transmission waveguides 104A, B may be substantially equal to an integral number of one-half wavelengths (nλ/2), for example. The ultrasonic transmission waveguides 104A, B may be preferably fabricated from a solid core shaft constructed out of material that propagates ultrasonic energy efficiently, such as titanium alloy (i.e., Ti-6Al-4V) or an aluminum alloy, for example.

FIG. 3A illustrates one embodiment of the ultrasonic transmission waveguide 104A positioned in an outer sheath 106A by a mounting O-ring 108A and a sealing ring 110A. One or more additional dampers or support members (not shown) also may be included along the ultrasonic transmission waveguide 104A. The ultrasonic transmission waveguide 104A is affixed to the outer sheath 106A by the isolator pin 112A that passes through mounting hole 114A in the outer sheath 106A and a mounting slot 116A in the ultrasonic transmission waveguide 104A.

FIG. 3B illustrates one embodiment of the ultrasonic transmission waveguide 104B positioned in an outer sheath 106B by a mounting O-ring 108B and a sealing ring 110B. One or more additional dampers or support members (not shown) also may be included along the ultrasonic transmission waveguide 104B. The ultrasonic transmission waveguide 104B is affixed to the outer sheath 106B by the isolator pin 112B that passes through mounting holes 114B in the outer sheath 106B and a mounting slot 116B in the ultrasonic transmission waveguide 104B.

Figure 4:
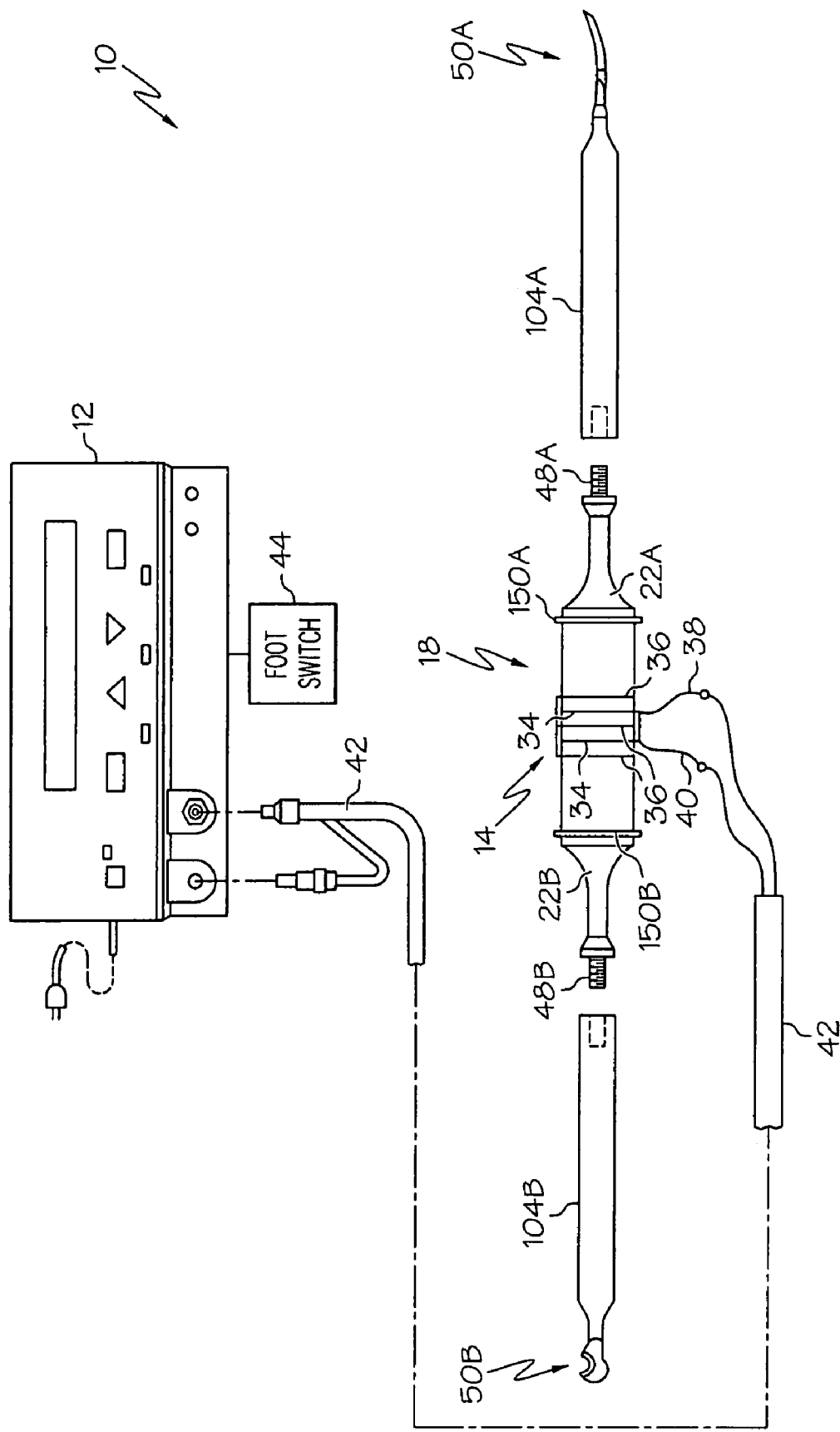
FIG. 4 is a simplified view of one embodiment of the ultrasonic system shown in FIG. 1.

FIG. 4 is a simplified schematic view of one embodiment of the ultrasonic system 10. For convenience and clarity, the handpiece assembly 60 illustrated in FIG. 4 is shown without the housing 16. The ultrasonic transducer 14 comprises the transduction portion 18 and the first and second resonator portions 22A, B. The first and second resonator portions 22A, B are coupled to the respective first second ultrasonic transmission waveguides 104A, B by the respective studs 48A, B. The first end effector 50A may comprise a blade, coagulator, or clamp that is different form the second end effector 50B. The transduction portion may be mounted to the housing 16 (FIG. 1) by flanges 150A, B. Each of the positive electrodes 34 and the negative electrodes 36 are electrically coupled to the wires 38 and 40, respectively. The wires 38 and 40 are encased within the cable 42 and electrically connectable to the ultrasonic signal generator 12 of the ultrasonic system 10. The transduction portion 18 of the hand assembly 60 may be energized by way of the foot switch 44.

FIGS. 5A, 5B, and 5C illustrate one embodiment of an ultrasonic instrument 500. The ultrasonic instrument 500 comprises first and second selectively deployable ultrasonically actuatable end effectors 50A and 50B coupled to the ultrasonic transducer 14. The transducer 14 is coupled to the ultrasonic signal generator 12 (FIGS. 1 and 4) through the cable 42. In the illustrated embodiments, the first and second end effectors 50A and 50B are shown as selectively deployable ultrasonically actuatable surgical blades, although the embodiments are not limited in this context. The ultrasonic transducer 14 is mounted to a transducer housing 512 via the mounting flanges 150A, B. The ultrasonic instrument 500 comprises an instrument housing 514. The transducer housing 512 and the instrument housing 514 are slideably attached and the transducer housing 512 bears against bearing surface 526 in an interior portion of the instrument housing 514. The instrument housing 514 comprises first and second shrouds 516A, B formed on first and second ends thereof to cover or contain the non-deployed end effector 50A, B. In the illustrated embodiment, the first end effector 50A is located in an active position and protrudes through the first shroud 516A through a first opening 520A and the second end effector 50B is located in a non-deployed position and is contained within the second shroud 516B. The instrument housing 514 is slideable and bears against the bearing surface 526 relative to the transducer housing 512 along the longitudinal axis 506 in either direction A or B.

The first end effector 50A may be deployed as the active end effector by sliding the instrument housing 514 in direction B relative to the transducer housing 512 until the first end effector 50A protrudes through the first opening 520A and is locked in place. Detents 522 formed on an interior wall 528 of the first and second shrouds 516A, B engage grooves or notches 524 formed on the transducer housing 512 to hold or lock the instrument housing 514 in place during use. The second end effector 50B may be deployed as the active end effector by sliding the instrument housing 514 in direction A relative to the transducer housing 512 until the second end effector 50B protrudes through a second opening 520B and is locked in place. Detents 522 formed on an interior wall 528 of the first and second shrouds 516A, B engage grooves or notches 524 formed on the transducer housing 512 to hold or lock the instrument housing 514 in place during use.

In one embodiment, the first end effector 50A comprises a first end 502A adapted to couple to one end of the ultrasonic transmission waveguide 104A and has at least a second end 502B suitable to cut, dissect, clamp, or coagulate organic tissue using energy in the form of mechanical vibrations transmitted through the ultrasonic transmission waveguide 104A at ultrasonic frequencies. The second end effector 50B comprises a first end 504A adapted to couple to one end of the ultrasonic transmission waveguide 104B and has at least a second end 504B suitable to cut, dissect, clamp, or coagulate organic tissue using energy in the form of mechanical vibrations transmitted through the ultrasonic transmission waveguide 104A at ultrasonic frequencies. In the illustrated embodiment, the first and second end effectors 50A, B comprise surgical blades with cutting and coagulating edges. The first and second end effectors 50A, B may be rotatable, articulatable, actuable, or otherwise controllable. The first and second end effectors 50A, B may be particularly suited for use in minimally invasive procedures, such as endoscopic or laparoscopic procedures, wherein either one of the first and second end effectors 50A, B may be passed through a trocar to reach a surgical site. Other suitable configurations for the first and second end effectors 50A, B may be employed. The embodiments are not limited in this context.

In one embodiment the ultrasonic surgical instrument 500 may comprise the transducer 14 previously described with reference to FIGS. 1 and 4 configured to produce vibrations along a longitudinal axis 506 at a predetermined ultrasonic frequency. The transducer 14 comprises first and second resonator portions 22A, B comprising respective first and second ends 508A, B adapted to couple ultrasonic energy to the respective first and second ultrasonic transmission waveguides 104A, B. The first ultrasonic transmission waveguide 104A is coupled to the first end 508A of the transducer 14 and extends along the longitudinal axis 506 in one direction. The second ultrasonic transmission waveguide 104B is coupled to the second end 508B of the transducer 14 and extends along the longitudinal axis 506 in an opposite direction from the first ultrasonic transmission waveguide 104A. The first and second ultrasonic transmission waveguides 104A, B may be configured to receive the selectable ultrasonically actuatable end effectors 50A, B. The distal end 502B, 504B of each of the first and second end effectors 50A, B is displaced relative to the longitudinal axis 506 by the mechanical vibrations produced by the transducer 14. The mechanical vibrations are transmitted to the either one of the active end effectors 50A, B at ultrasonic frequencies. The embodiments are not limited in this context.

In one embodiment, the transducer 14 is adapted to couple to the two active ultrasonic transmission waveguides 104A, B (e.g., horns) and the respective mounting studs 510A, B to enable mounting and simultaneously vibrating the first and second end effectors 50A, B. One of the end effectors 50A, B generally will be the active end effector employed at any given time. In the embodiment illustrated in FIGS. 5A-C, the first end effector 50A is active and protrudes from the shroud 516A through the first opening 520A and the second end effector 50B is non-deployed and is stowed within the shroud 561B. In one embodiment, the end effectors 50A, B (e.g., the surgical cutting and/or coagulating blades) may have a relatively short and delicate form factor and may be suitable for use in fine and delicate spinal surgeries. The non-deployed end effector 50B consumes minimal power and generates minimal heat. Minimal power consumption may be obtained from a suitable design of the end effector 50A, B, which comprises selection of adequate end effector mechanical gain, overall mass, length, and suitable material. Furthermore, the non-deployed end effector 50B consumes minimal quiescent ultrasonic power also due to the fact that it is not loaded by tissue, thereby generating substantially low quiescent heat due to loading. As described and illustrated herein, the non-deployed blade at the second end 504B is contained within the shroud 516B when not in use. This protects the non-deployed end effector 50B from contacting unwanted objects. In one embodiment, the electrical operation of the ultrasonic instrument 500 may be inhibited when both end effectors 50A, B are exposed. This may occur, for example, in a transitional phase while sliding the instrument housing 514 in either direction A or B to switch from one of the end effectors 50A, B to the other.

As described herein, one embodiment of the ultrasonic instrument 500 may be operated with one hand 518 and may be adapted for delicate surgeries such as spinal surgeries involving diskectomies, for example. During such delicate surgeries, the surgeon can readily switch between the first and second end effectors 50A, B by sliding the instrument housing 512 relative to the transducer housing 514 either in direction A or B. The embodiments are not limited in this context.

FIGS. 6A, 6B, and 6C illustrate one embodiment of an ultrasonic instrument 600. The ultrasonic instrument 600 comprises first and second selectively deployable ultrasonically actuatable end effectors 50A and 50B (e.g., selectively deployable ultrasonically actuatable surgical blades in the illustrated embodiment) coupled to the ultrasonic transducer 14. The transducer 14 is coupled to the ultrasonic signal generator 12 (FIGS. 1 and 4) through the cable 42. The ultrasonic transducer 14 is mounted within a transducer housing (not shown) by the mounting flanges 150A, B. The ultrasonic instrument 600 comprises an instrument housing 614. The ultrasonic instrument 600 comprises a slide switch 630. The slide switch 630 is coupled to a first tube 634A by a first linkage 632A and to a second tube 634B by a second linkage 632B. The instrument housing 614 is slideably engaged with the first and second tubes 634A, B and bears against bearing surfaces 636A, B. The first and second tubes 634A, B cover or contain whichever one of the end effectors 50A, B is not deployed. As shown in the illustrated embodiment, the first end effector 50A is the active end effector and protrudes from the first tube 634A through a first opening 620A. As shown in the illustrated embodiment, the second end effector 50B is the non-deployed end effector and is contained within the second tube 634B. The slide switch 630 is slideable along the longitudinal axis 506 in either direction A or B to position the first and second tubes 634A, B to expose the active end effector 50A and to protect or cover the non-deployed end effector 50B.

The first end effector 50A may be deployed as the active end effector by sliding the switch 630 in direction B to retract the first tube 634A substantially within the instrument housing 614 until the first end effector 50A protrudes through the first opening 620A. The first end effector then may be locked in place for use. The second end effector 50B may be deployed as the active end effector by sliding the switch 630 in direction A to retract the second tube 634B substantially within the instrument housing 614 until the second end effector 50B protrudes through a second opening 620B. The second end effector is locked in place for use.

In one embodiment, the first end effector 50A comprises a first end 602A adapted to couple to one end of the ultrasonic transmission waveguide 104A and has at least a second end 602B suitable to cut, dissect, clamp, or coagulate organic tissue using energy in the form of mechanical vibrations transmitted through the ultrasonic transmission waveguide 104A at ultrasonic frequencies. The second end effector 50B comprises a first end 604A adapted to couple to one end of the ultrasonic transmission waveguide 104B and has at least a second end 604B suitable to cut, dissect, clamp, or coagulate organic tissue using energy in the form of mechanical vibrations transmitted through the ultrasonic transmission waveguide 104A at ultrasonic frequencies. In the illustrated embodiment, the first and second end effectors 50A, B comprise surgical blades with cutting and coagulating edges. The first and second end effectors 50A, B may be rotatable, articulatable, actuable, or otherwise controllable. The first and second end effectors 50A, B may be particularly suited for use in minimally invasive procedures, such as endoscopic or laparoscopic procedures, wherein either one of the first and second end effectors 50A, B may be passed through a trocar to reach a surgical site. Other suitable configurations for the first and second end effectors 50A, B may be employed. The embodiments are not limited in this context.

In one embodiment the ultrasonic surgical instrument 600 comprises the transducer 14 previously described with reference to FIGS. 1 and 4 configured to produce vibrations along a longitudinal axis 506 at a predetermined ultrasonic frequency. The transducer 14 comprises first and second resonator portions 22A, B comprising respective first and second ends 608A, B adapted to couple ultrasonic energy to the respective first and second ultrasonic transmission waveguides 104A, B. The first ultrasonic transmission waveguide 104A is coupled to the first end 608A of the transducer 14 and extends along the longitudinal axis 506 in one direction. The second ultrasonic transmission waveguide 104B is coupled to the second end 608B of the transducer 14 and extends along the longitudinal axis 506 in an opposite direction from the first ultrasonic transmission waveguide 104A. The first and second ultrasonic transmission waveguides 104A, B may be configured to receive the ultrasonically actuatable end effectors 50A, B. The distal ends 602B, 604B of each of the first and second end effectors 50A, B is displaced relative to the longitudinal axis 506 by the mechanical vibrations produced by the transducer 14. The mechanical vibrations are transmitted to the either one of the active end effectors 50A, B at ultrasonic frequencies. The embodiments are not limited in this context.

In one embodiment, the transducer 14 is adapted to couple to two active ultrasonic transmission waveguides 104A, B (e.g., horns) and respective mounting studs 510A, B to enable mounting and simultaneously vibrating the first and second end effectors 50A, B. One of the end effectors 50A, B generally will be the active end effector employed at any given time. In the embodiment illustrated in FIGS. 6A-C, the first end effector 50A is active and protrudes from the first tube 634A through the first opening 620A and the second end effector 50B is not deployed and stowed within the second tube 634B. In one embodiment, the end effectors 50A, B (e.g., the surgical cutting and/or coagulating blades) may have a relatively short and delicate form factor and may be suitable for use in fine and delicate spinal surgeries. The non-deployed end effector 50B consumes minimal power and generates minimal heat. As described and illustrated herein, the non-deployed blade at the second end 604B is contained within the second tube 634B when not in use. This protects the non-deployed end effector 50B from contacting unwanted objects. In one embodiment, the electrical operation of the ultrasonic instrument 600 may be inhibited when both end effectors 50A, B are exposed. This may occur, for example, in a transitional phase while sliding the switch 630 in either direction A or B to switch from one of the end effectors 50A, B to the other.

As described herein, one embodiment of the ultrasonic instrument 600 may be operated with one hand 518 and may be adapted for delicate surgeries such as spinal surgeries involving diskectomies, for example. During such delicate surgeries, the surgeon can readily switch between the first and second end effectors 50A and 50B by sliding the slide switch 630 in either direction A or B. The embodiments are not limited in this context.

FIGS. 7A, 7B, and 7C illustrate one embodiment of an ultrasonic instrument 700. The ultrasonic instrument 700 comprises first and second selectively deployable ultrasonically actuatable end effectors 50A and 50B (e.g., ultrasonically actuatable surgical blades in the illustrated embodiment) coupled to the ultrasonic transducer 14. The transducer 14 is coupled to the ultrasonic signal generator 12 (FIGS. 1 and 4) through the cable 42. The ultrasonic transducer 14 is mounted within a transducer housing (not shown) by the mounting flanges 150A, B. The ultrasonic instrument 700 comprises an instrument housing 714. The ultrasonic instrument 700 comprises first and second rotatable grips 730A, 730B. The grips 730A, B are rotatable on threaded portions 732A, 732B of respective tubes 734A, 734B. As the rotatable grips 730A, B are rotated on the respective threaded tubes 734A, B, the threaded tubes 734A, B are slideable along the longitudinal axis 506 in either direction A or B to either reveal the active end effector 50A (as shown) for use or to cover or contain the non-deployed end effector 50B (as shown) when not in use. The first and second tubes 734A, B cover or contain the non-deployed end effector 50A, B. As shown in the illustrated embodiment, the first end effector 50A is active and protrudes from the first tube 734A through a first opening 720A. As shown in the illustrated embodiment, the second end effector 50B is not deployed and is contained within the second tube 734B.

The first end effector 50A may be deployed as the active end effector by threading the first rotatable grip 730A about the threaded tube 734A in a clockwise direction to slideably move the threaded tube 734A in direction B along the longitudinal axis 506. Accordingly, the first tube 734A will be retracted substantially within the instrument housing 714 until the first end effector 50A protrudes from the threaded tube 734A through the first opening 720A and is exposed for use. The second end effector 50B may be deployed as the active end effector by threading the second rotatable grip 732B about the threaded tube 734B in a clockwise direction to slideably move the threaded tube 734B in direction A along the longitudinal axis 506. Accordingly, the second threaded tube 732B will be retracted substantially within the instrument housing 714 until the second end effector 50B protrudes from the second opening 720B and is exposed for use.

In one embodiment, the first end effector 50A comprises a first end 702A adapted to couple to one end of the ultrasonic transmission waveguide 104A and has at least a second end 702B suitable to cut, dissect, clamp, or coagulate organic tissue using energy in the form of mechanical vibrations transmitted through the ultrasonic transmission waveguide 104A at ultrasonic frequencies. The second end effector 50B comprises a first end 704A adapted to couple to one end of the ultrasonic transmission waveguide 104B and has at least a second end 704B suitable to cut, dissect, clamp, or coagulate organic tissue using energy in the form of mechanical vibrations transmitted through the ultrasonic transmission waveguide 104A at ultrasonic frequencies. In the illustrated embodiment, the first and second end effectors 50A, B comprise surgical blades with cutting and coagulating edges. The first and second end effectors 50A, B may be rotatable, articulatable, actuable, or otherwise controllable. The first and second end effectors 50A, B may be particularly suited for use in minimally invasive procedures, such as endoscopic or laparoscopic procedures, wherein either one of the first and second end effectors 50A, B may be passed through a trocar to reach a surgical site. Other suitable configurations for the first and second end effectors 50A, B may be employed. The embodiments are not limited in this context.

In one embodiment the ultrasonic surgical instrument 700 comprises the transducer 14 previously described with reference to FIGS. 1 and 4 configured to produce vibrations along a longitudinal axis 506 at a predetermined ultrasonic frequency. The transducer 14 comprises first and second resonator portions 22A, B comprising respective first and second ends 708A, B adapted to couple ultrasonic energy to the respective first and second ultrasonic transmission waveguides 104A, B. The first ultrasonic transmission waveguide 104A is coupled to the first end 708A of the transducer 14 and extends along the longitudinal axis 506 in one direction. The second ultrasonic transmission waveguide 104B is coupled to the second end 708B of the transducer 14 and extends along the longitudinal axis 506 in an opposite direction from the first ultrasonic transmission waveguide 104A. The first and second ultrasonic transmission waveguides 104A, B may be configured to receive the ultrasonically actuatable end effectors 50A, B. The distal ends 702B, 704B of each of the first and second end effectors 50A, B is displaced relative to the longitudinal axis 506 by the mechanical vibrations produced by the transducer 14. The mechanical vibrations are transmitted to the either one of the active end effectors 50A, B at ultrasonic frequencies. The embodiments are not limited in this context.

In one embodiment, the transducer 14 is adapted to couple to two active ultrasonic transmission waveguides 104A, B (e.g., horns) and respective mounting studs 510A, B to enable mounting and simultaneously vibrating the first and second end effectors 50A, B. One of the end effectors 50A, B generally will be the active end effector employed at any given time. In the embodiment illustrated in FIGS. 7A-C, the first end effector 50A is the active end effector protruding through the first tube 734A and the first opening 720A and the second end effector 50B is not deployed and stowed within the second tube 734B. In one embodiment, the end effectors 50A, B (e.g., the surgical cutting and/or coagulating blades) may have a relatively short and delicate form factor and may be suitable for use in fine and delicate spinal surgeries. The non-deployed end effector 50B consumes minimal power and generates minimal heat when not in use. As described and illustrated herein, the non-deployed blade at the second end 704B is contained within the second tube 734B when not in use for safety purposes. In one embodiment, the electrical operation of the ultrasonic instrument 700 may be inhibited when both end effectors 50A, B are exposed. This may occur, for example, if both threaded tubes 730A, B are rotated to expose the respective end effectors 50A, B when switching from using one of the end effectors 50A, B to the other.

As described herein, one embodiment of the ultrasonic instrument 700 may be operated with one hand 518 and may be adapted for delicate surgeries such as spinal surgeries involving diskectomies, for example. During such delicate surgeries, the surgeon can readily switch between the first and second end effector 50A, B by rotating the rotatable grips 730A, B and sliding the threaded tubes 734A, B either in direction A or B to expose the active end effector (50A as shown) and cover the non-deployed end effector (50B as shown). The embodiments are not limited in this context.

FIGS. 8A, 8B, and 8C illustrate one embodiment of an ultrasonic instrument 800. The ultrasonic instrument 800 comprises first and second selectively deployable ultrasonically actuatable end effectors 50A and 50B (e.g., ultrasonically actuatable surgical blades in the illustrated embodiment) coupled to the ultrasonic transducer 14. The transducer 14 is coupled to the ultrasonic signal generator 12 (FIGS. 1 and 4) through the cable 42. The ultrasonic transducer 14 is mounted within a transducer housing (not shown) by the mounting flanges 150A, B. The ultrasonic instrument 800 comprises an instrument housing 814. The ultrasonic instrument 800 comprises a cam 816. The cam 816 includes a guide pin 822 to guide the cam in an arcuate slot 818 formed in the housing 814. When a force is applied to move the cam 816 in direction A, the cam 816 rotates about a pivot 819 and the guide pin 822 engages the slot 818. Accordingly, the cam 816 moves from a first position 824A to a second position 824B (shown in phantom). The cam 816 is coupled to first and second tubes 834A, B by a linkage 832. The linkage 832 comprises a first portion 832A coupled to the first tube 834A and a second portion 832B coupled to the second tube 834B. The first and second tubes 834A, B are slideably received within the instrument housing 814 and bear against bearing surfaces 836A, B in an interior portion of the housing 814. The first and second tubes 834A, B cover or contain whichever one of the end effectors 50A, B is not deployed. In the illustrated embodiment, the first end effector 50A is active and protrudes from the first tube 834A through a first opening 820A. In the illustrated embodiment, the second end effector 50B is not deployed and is contained within the second tube 834B. The cam 816 is rotatable within the slot 818 about the pivot point 819 to slide the first and second tubes 834A, B along the longitudinal axis 506 in either direction A or B to position the first and second tubes 834A, B to either expose the first end effector 50A (active) and protect or cover the second end effector 50B (non-deployed), as shown in the illustrated embodiment, or to expose the second end effector 50B and protect or cover the first end effector 50A.

The first end effector 50A may be deployed as the active end effector by sliding the cam 816 in direction B to retract the first tube 834A along the longitudinal axis 506 until it is substantially located within the instrument housing 814, the first end effector 50A protrudes from the first opening 820A and is exposed for use. The second end effector 50B may be deployed as the active end effector by sliding the cam 816 in direction A to retract the second tube 834B along longitudinal axis 506 until it is substantially located within the instrument housing 814, the second end effector 50B protrudes from a second opening 820B and is exposed for use. The embodiments are not limited in this context.

In one embodiment, the first end effector 50A comprises a first end 802A adapted to couple to one end of the ultrasonic transmission waveguide 104A and has at least a second end 802B suitable to cut, dissect, clamp, or coagulate organic tissue using energy in the form of mechanical vibrations transmitted through the ultrasonic transmission waveguide 104A at ultrasonic frequencies. The second end effector 50B comprises a first end 804A adapted to couple to one end of the ultrasonic transmission waveguide 104B and has at least a second end 804B suitable to cut, dissect, clamp, or coagulate organic tissue using energy in the form of mechanical vibrations transmitted through the ultrasonic transmission waveguide 104A at ultrasonic frequencies. In the illustrated embodiment, the first and second end effectors 50A, B comprise surgical blades with cutting and coagulating edges. The first and second end effectors 50A, B may be rotatable, articulatable, actuable, or otherwise controllable. The first and second end effectors 50A, B may be particularly suited for use in minimally invasive procedures, such as endoscopic or laparoscopic procedures, wherein either one of the first and second end effectors 50A, B may be passed through a trocar to reach a surgical site. The embodiments are not limited in this context.

In one embodiment the ultrasonic surgical instrument 800 comprises the transducer 14 previously described with reference to FIGS. 1 and 4 configured to produce vibrations along a longitudinal axis 506 at a predetermined ultrasonic frequency. The transducer 14 comprises first and second resonator portions 22A, B comprising respective first and second ends 808A, B adapted to couple ultrasonic energy to the respective first and second ultrasonic transmission waveguides 104A, B. The first ultrasonic transmission waveguide 104A is coupled to the first end 808A of the transducer 14 and extends along the longitudinal axis 506 in one direction. The second ultrasonic transmission waveguide 104B is coupled to the second end 808B of the transducer 14 and extends along the longitudinal axis 506 in an opposite direction from the first ultrasonic transmission waveguide 104A. The first and second ultrasonic transmission waveguides 104A, B may be configured to receive the ultrasonically actuatable end effectors 50A, B. The distal ends 802B, 804B of each of the first and second end effectors 50A, B is displaced relative to the longitudinal axis 506 by the mechanical vibrations produced by the transducer 14. The mechanical vibrations are transmitted to the either one of the active end effectors 50A, B at ultrasonic frequencies. The embodiments are not limited in this context.

In one embodiment, the transducer 14 is adapted to couple to two active ultrasonic transmission waveguides 104A, B (e.g., horns) and respective mounting studs 510A, B to enable mounting and simultaneously vibrating the first and second end effectors 50A, B. One of the end effectors 50A, B generally will be the active end effector employed at any given time. In the embodiment illustrated in FIGS. 8A-C, the first end effector 50A is the active end effector protruding through the first tube 834A and the first opening 820A and the second end effector 50B is not deployed and stowed within the second tube 834B. In one embodiment, the end effectors 50A, B (e.g., the surgical cutting and/or coagulating blades) may have a relatively short and delicate form factor and may be suitable for use in fine and delicate spinal surgeries. The non-deployed end effector 50B consumes minimal power and generates minimal heat. As described and illustrated herein, the non-deployed blade at the second end 804B is contained within the second tube 834B when not in use. This protects the non-deployed end effector 50B from contacting unwanted objects. In one embodiment, the electrical operation of the ultrasonic instrument 800 may be inhibited when both end effectors 50A, B are exposed. This may occur, for example, in a transitional phase when switching from using one of the end effectors 50A, B to the other.

As described herein, one embodiment of the ultrasonic instrument 800 may be operated with one hand 518 and may be adapted for delicate surgeries such as spinal surgeries involving diskectomies, for example. During such delicate surgeries, the surgeon may readily switch between the first and second end effectors 50A, B by rotating the cam 816 and sliding the tubes 834A, B either in direction A or B to position either one of the first and second tubes 834A, B to cover the desired end effector or to expose the desired end effector. The embodiments are not limited in this context.

FIGS. 9A, 9B, and 9C illustrate one embodiment of an ultrasonic instrument 900. The ultrasonic instrument 900 comprises first and second selectively deployable ultrasonically actuatable end effectors 50A and 50B (e.g., ultrasonically actuatable surgical blades in the illustrated embodiment) coupled to the ultrasonic transducer 14. The ultrasonic transducer 14 is mounted within a transducer housing (not shown) by the mounting flanges 150A, B. The ultrasonic instrument 900 comprises an instrument housing 914. The ultrasonic instrument 900 comprises a cap 934 to protect either one of the first and second end effectors 50A and 50B. The cap 934 is received by either one of a first or second sleeve 932A, B. The cap 934 is removably attached to either of the first and second sleeves 932A, B to cover the corresponding first or second end effector 50A, B. To cover the first end effector 50A, the cap 934 is slidingly inserted over the first sleeve 932A in direction B. To cover the second effector 50B, the cap 934 is slidingly inserted over the second sleeve 932B in direction A. In the illustrated embodiment, the first end effector 50A is active and remains exposed for use. In the illustrated embodiment, the second end effector 50B is not deployed.

The first end effector 50A may be deployed as the active end effector by removing the cap 934 from the first sleeve 932A (if it was initially inserted over the first sleeve 932A). Once removed, the cap 934 is slidingly inserted over the second sleeve 932B in direction A. The second end effector 50B may be deployed as the active end effector, the cap 934 is slidingly removed from the second sleeve 932B in direction B and slidingly inserting the cap 934 over the first sleeve 932A in direction B to cover the first end effector 50A and expose the second effector 50B for use.

In one embodiment, the first end effector 50A comprises a first end 902A adapted to couple to one end of the ultrasonic transmission waveguide 104A and has at least a second end 902B suitable to cut, dissect, clamp, or coagulate organic tissue using energy in the form of mechanical vibrations transmitted through the ultrasonic transmission waveguide 104A at ultrasonic frequencies. The second end effector 50B comprises a first end 904A adapted to couple to one end of the ultrasonic transmission waveguide 104B and has at least a second end 904B suitable to cut, dissect, clamp, or coagulate organic tissue using energy in the form of mechanical vibrations transmitted through the ultrasonic transmission waveguide 104A at ultrasonic frequencies. In the illustrated embodiment, the first and second end effectors 50A, B comprise surgical blades with cutting and coagulating edges. The first and second end effectors 50A, B may be rotatable, articulatable, actuable, or otherwise controllable. The first and second end effectors 50A, B may be particularly suited for use in minimally invasive procedures, such as endoscopic or laparoscopic procedures, wherein either one of the first and second end effectors 50A, B may be passed through a trocar to reach a surgical site. The embodiments are not limited in this context.

In one embodiment the ultrasonic surgical instrument 900 comprises the transducer 14 previously described with reference to FIGS. 1 and 4 configured to produce vibrations along a longitudinal axis 506 at a predetermined ultrasonic frequency. The transducer 14 is coupled to the ultrasonic signal generator 12 (FIGS. 1 and 4) through the cable 42. The transducer 14 comprises first and second resonator portions 22A, B comprising respective first and second ends 908A, B adapted to couple ultrasonic energy to the respective first and second ultrasonic transmission waveguides 104A, B. The first ultrasonic transmission waveguide 104A is coupled to the first end 908A of the transducer 14 and extends along the longitudinal axis 506 in one direction. The second ultrasonic transmission waveguide 104B is coupled to the second end 908B of the transducer 14 and extends along the longitudinal axis 506 in an opposite direction from the first ultrasonic transmission waveguide 104A. The first and second ultrasonic transmission waveguides 104A, B may be configured to receive the ultrasonically actuatable end effectors 50A, B. The distal ends 902B, 904B of each of the first and second end effectors 50A, B is displaced relative to the longitudinal axis 506 by the mechanical vibrations produced by the transducer 14. The mechanical vibrations are transmitted to the either one of the active end effectors 50A, B at ultrasonic frequencies. The embodiments are not limited in this context.

In one embodiment, the transducer 14 is adapted to couple to two active ultrasonic transmission waveguides 104A, B (e.g., horns) and respective mounting studs 510A, B arrangement to enable mounting and simultaneously vibrating the first and second end effectors 50A, B. One of the end effectors 50A, B generally will be the active end effector employed at any given time. In the embodiment illustrated in FIGS. 9A-C, the first end effector 50A is the active end effector protruding through the first sleeve 932A and first opening 920A and the second end effector 50B is non-deployed and stowed within the second sleeve 932B through second opening 920B. In one embodiment, the end effectors 50A, B (e.g., the surgical cutting and/or coagulating blades) may have a relatively short and delicate form factor and may be suitable for use in fine and delicate spinal surgeries. In such an embodiment, the non-deployed end effector SOB consumes minimal power and generates minimal heat. As described herein, the non-deployed blade at the second end 904B is contained within the second sleeve 932B when not in use for safety purposes. In one embodiment, the electrical operation of the ultrasonic instrument 900 may be inhibited when both end effectors 50A, B are exposed. This may occur, for example, in a transitional phase while replacing the cap 934 from one side of the instrument housing 914 to the other when switching from one end effector to another.

As described herein, one embodiment of the ultrasonic instrument 900 may be operated with one hand 518 and may be adapted for delicate surgeries such as spinal surgeries involving diskectomies, for example. During such delicate surgeries, the surgeon may readily exchange between the first and second end effectors 50A and 50B by removing the cap 934 from either one of the first or second sleeve 932A, B and inserting it over the opposite sleeve 932B, A to expose the desired end effector 50A and to cover the other end effector 50B. The embodiments are not limited in this context.

The devices disclosed herein can be designed to be disposed of after a single use, or they can be designed to be used multiple times. In either case, however, the device may be reconditioned for reuse after at least one use. Reconditioning can include any combination of the steps of disassembly of the device, followed by cleaning or replacement of particular elements, and subsequent reassembly. In particular, the device may be disassembled, and any number of particular elements or components of the device may be selectively replaced or removed in any combination. Upon cleaning and/or replacement of particular components, the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
a transducer defining a longitudinal axis, the transducer comprising a first end and a second end, the transducer further comprising:
a transduction portion disposed along the longitudinal axis and comprising a first end and a second end, the transduction portion configured to produce vibration in a first direction along the longitudinal axis at a predetermined frequency, the transduction portion configured to produce vibrations in a second direction along the longitudinal axis at the predetermined frequency, wherein the second direction is substantially opposite the first direction;
a first resonator portion disposed along the longitudinal axis and configured to receive ultrasonic vibration in the first direction from the first end of the transduction portion, the first resonator portion comprising a first end coupled to the first end of the transduction portion and a second end adapted to receive the first ultrasonic transmission waveguide;
a first ultrasonic transmission waveguide disposed along the longitudinal axis and configured to receive ultrasonic vibrations in the first direction from the second end of the first resonator portion, the first ultrasonic transmission waveguide comprising a first end coupled to the second end of the first resonator portion;
a first deployable ultrasonic end effector disposed along the longitudinal axis coupled to a second end of the first ultrasonic transmission waveguide;
a second resonator portion disposed along the longitudinal axis and configured to receive ultrasonic vibration in the second direction from the second end of the transduction portion, the second resonator portion comprising a first end coupled to the second end of the transduction portion and a second end adapted to receive a second ultrasonic transmission waveguide;
a second ultrasonic transmission waveguide disposed along the longitudinal axis and configured to receive ultrasonic vibrations in the second direction from the second end of the second resonator portion, the second ultrasonic transmission waveguide comprising a first end coupled to the second end of the second resonator portion;

a second deployable ultrasonic end effector disposed along the longitudinal axis coupled to a second end of the second ultrasonic transmission waveguide;

wherein, when the first resonator portion receives ultrasonic vibrations in the first direction, the second resonator portion receives ultrasonic vibrations in the second direction;

wherein, when one of the deployable ultrasonic end effectors is deployed, the other deployable ultrasonic end effector is non-deployed to prevent contact with unwanted objects; and wherein, when the deployed deployable ultrasonic end effector is loaded by tissue the non-deployed deployable ultrasonic end effector is unloaded by tissue and consumes less power and generates less heat than the deployed ultrasonic end effector.

2. The surgical instrument of claim 1, comprising:
a transducer housing; and
an instrument housing having a first end and a second end, the instrument housing is slideably attached to the transducer housing, wherein the transducer housing bears against a bearing surface of the instrument housing, the instrument housing comprising:
a first shroud formed on the first end of the instrument housing, the first shroud defining an opening to receive the first end effector therein; and
a second shroud formed on the second end of the instrument housing, the second shroud defining an opening to receive the second end effector therein.

3. The surgical instrument of claim 2, wherein the instrument housing is slideable to:
a first position to contain the second end effector within the second shroud and expose the first end effector through the opening defined by the first shroud; and
wherein the instrument housing is slideable to:
a second position to contain the first end effector within the first shroud and expose the second end effector through the opening defined by the second shroud.

4. The surgical instrument of claim 1, wherein the surgical device is configured to receive a first end effector movable by ultrasonic vibrations propagating from first end of the transducer and further configured to receive a second end effector movable by ultrasonic vibrations propagating from the second end of the transducer.

5. A method for processing a surgical instrument for surgery, comprising:
obtaining the surgical instrument of claim 1;
attaching at least one ultrasonic transmission waveguide to the at least one of the first resonator or the second resonator portions; and
sterilizing the surgical instrument.

6. A surgical system, comprising:
a transducer housing;
a transducer coupled to the ultrasonic signal generator, the transducer defining a longitudinal axis, the transducer comprising a first end, a second end, a transduction portion, a first resonator portion, and a second resonator portion;
the transduction portion disposed along the longitudinal axis and comprising a first end, a plurality of piezoelectric elements arranged in a stack to form a piezoelectric stack, and a second end, the piezoelectric stack comprising a bore through which a coupling member extends, the piezoelectric stack configured to produce vibrations in a first direction and a second direction along the longitudinal axis at a predetermined frequency, wherein the second direction is substantially opposite to the first direction, and the transduction portion mounted to the transducer housing by at least two flanges;

the first resonator portion disposed along the longitudinal axis and configured to receive ultrasonic vibration in the first direction from the first end of the transduction portion;

the first ultrasonic transmission waveguide comprising a first end coupled to the second end of the first resonator portion;

the second resonator portion disposed along the longitudinal axis and configured to receive ultrasonic vibrations in the second direction from the second end of the transduction portion; the second resonator portion comprises a first end coupled to the coupling member at the second end of the transduction portion and a second end adapted to receive a second ultrasonic transmission waveguide; and a second ultrasonic transmission waveguide disposed along the longitudinal axis and configured to receive ultrasonic vibrations in the second direction from the second end of the second resonator portion, the second ultrasonic transmission waveguide comprising a first end coupled to the second end of the second resonator portion;

wherein, when one resonator portion receives ultrasonic vibrations in the first direction, the other resonator portion receives ultrasonic vibrations in the second direction.

7. The surgical system of claim 6, comprising:
a first ultrasonic end effector extending along the longitudinal axis coupled to a second end of the first ultrasonic transmission waveguide; and
a second ultrasonic end effector extending along the longitudinal axis coupled to a second end of the ultrasonic transmission waveguide.

8. The surgical system of claim 7, wherein the first and second ultrasonic end effectors are deployable in substantially opposite directions along the longitudinal axis.

9. A surgical instrument, comprising:
a transducer defining a longitudinal axis, the transducer comprising a first end and a second end, the transducer further comprising:
a transduction portion disposed along the longitudinal axis and comprising a first end and a second end, the transduction portion configured to produce vibrations in a first direction along the longitudinal axis at a predetermined frequency, the transduction portion configured to produce vibrations in a second direction along the longitudinal axis at the predetermined frequency, the second direction substantially opposite to the first direction;
a first resonator portion disposed along the longitudinal axis and configured to receive ultrasonic vibration in the first direction from the first end of the transduction portion, the first resonator portion comprising a first end coupled to the first end of the transduction portion and a second end adapted to receive a first ultrasonic transmission waveguide;
a first ultrasonic transmission waveguide disposed along the longitudinal axis and configured to receive ultrasonic vibrations in the first direction from the second end of the first resonator portion, the first ultrasonic transmission waveguide comprising a first end coupled to the second end of the first resonator portion;

a first deployable ultrasonic end effector disposed along the longitudinal axis coupled to a second end of the first ultrasonic transmission waveguide, the first deployable ultrasonic end effector movable from a deployed position to a non-deployed position;

a second resonator portion disposed along the longitudinal axis and configured to receive ultrasonic vibration in the second direction from the second end of the transduction portion, the second resonator portion comprising a first end coupled to the second end of the transduction portion and a second end adapted to receive a second ultrasonic transmission waveguide;

a second ultrasonic transmission waveguide disposed along the longitudinal axis and configured to receive ultrasonic vibrations in the second direction from the second end of the second resonator portion, the second ultrasonic transmission waveguide comprising a first end coupled to the second end of the second resonator portion;

a second deployable ultrasonic end effector disposed along the longitudinal axis coupled to a second end of the second ultrasonic transmission waveguide, the second deployable ultrasonic end effector movable from a deployed position to a non-deployed position;

wherein, when the first resonator portion receives ultrasonic vibrations in the first direction, the second resonator portion receives ultrasonic vibrations in the second direction;

wherein, when one of the deployable ultrasonic end effectors is deployed, the other deployable ultrasonic end effector is non-deployed to prevent contact with unwanted objects; and wherein, when the deployed deployable ultrasonic end effector is loaded by tissue the non-deployed deployable ultrasonic end effector is unloaded by tissue and consumes less power and generates less heat than the deployed ultrasonic end effector.

* * * * *